(12) United States Patent
Morrell et al.

(10) Patent No.: US 11,138,865 B1
(45) Date of Patent: Oct. 5, 2021

(54) CANINE EMERGENCY ALERT SYSTEM

(71) Applicant: Priority 1 Canine, LLC, Thornville, OH (US)

(72) Inventors: Wade Morrell, Thornville, OH (US); Lori Morrell, Thornville, OH (US)

(73) Assignee: PRIORITY 1 CANINE, LLC, Thornville, OH (US)

( * ) Notice: Subject to any disclaimer, the term of this patent is extended or adjusted under 35 U.S.C. 154(b) by 0 days.

(21) Appl. No.: 17/223,118

(22) Filed: Apr. 6, 2021

Related U.S. Application Data

(60) Provisional application No. 63/006,183, filed on Apr. 7, 2020.

(51) Int. Cl.

| | |
|---|---|
| G08B 25/01 | (2006.01) |
| G08B 25/00 | (2006.01) |
| G08B 21/04 | (2006.01) |
| G01S 19/17 | (2010.01) |
| G08B 5/00 | (2006.01) |
| G08B 5/36 | (2006.01) |
| G08B 3/10 | (2006.01) |

(52) U.S. Cl.
CPC ............ *G08B 25/016* (2013.01); *G01S 19/17* (2013.01); *G08B 3/10* (2013.01); *G08B 5/002* (2013.01); *G08B 5/36* (2013.01); *G08B 21/043* (2013.01); *G08B 21/0461* (2013.01); *G08B 25/008* (2013.01)

(58) Field of Classification Search
CPC .................................................... G08B 25/16
See application file for complete search history.

(56) References Cited

U.S. PATENT DOCUMENTS

| | | | |
|---|---|---|---|
| 4,924,214 | A | 5/1990 | Hill |
| 5,604,478 | A | 2/1997 | Grady et al. |
| 6,123,049 | A | 9/2000 | Slater |

(Continued)

FOREIGN PATENT DOCUMENTS

| | | |
|---|---|---|
| WO | 2018213615 A2 | 11/2018 |
| WO | 2019023037 A1 | 1/2019 |

OTHER PUBLICATIONS

Interntional Search Report and Written Opinion; PCT/US21/26187; dated Jul. 15, 2021; 7 pages.

(Continued)

*Primary Examiner* — Travis R Hunnings
(74) *Attorney, Agent, or Firm* — Dickinson Wright PLLC

(57) ABSTRACT

An emergency alert system and method of operation are provided. The system includes an emergency alert pad configured to detect a pad activation by a service animal and communicate a pad alert in response. An emergency alert vest is worn by the service animal and is configured to detect a vest activation by a person in proximity and communicate a vest alert in response. A user mobile device is in communication with the emergency alert pad and vest and is configured to record a pre-recorded message. At least one affiliated mobile device is configured to receive the pre-recorded message during the pad activation and the vest activation. An emergency response center is in communication with the emergency alert pad and the emergency alert vest and is configured to receive at least one of the pad alert and the vest alert and provide emergency services accordingly.

20 Claims, 24 Drawing Sheets

(56) References Cited

U.S. PATENT DOCUMENTS

| | | |
|---|---|---|
| 7,057,515 B2 | 6/2006 | Smith et al. |
| 7,281,363 B2 | 10/2007 | Woerner |
| 7,332,686 B2 | 2/2008 | Parnell |
| 7,439,463 B2 | 10/2008 | Brenner et al. |
| D585,606 S | 1/2009 | Kennedy |
| 7,609,155 B2 | 10/2009 | HinKamp |
| 7,762,953 B2 | 7/2010 | Derchak et al. |
| 7,918,192 B1 | 4/2011 | Digh et al. |
| D699,758 S | 2/2014 | Lavin et al. |
| 9,031,714 B1 | 5/2015 | Everett et al. |
| D745,748 S | 12/2015 | Tacker-Betancourt |
| 9,666,062 B1 | 5/2017 | Rachal |
| 9,826,712 B2 | 11/2017 | Lipscomb et al. |
| 10,034,457 B2 * | 7/2018 | Swartz ................. A01K 15/021 |
| 10,178,854 B1 | 1/2019 | Lawson et al. |
| 10,342,217 B2 | 7/2019 | Brown |
| 10,997,850 B1 * | 5/2021 | Clark ..................... A01K 29/00 |
| 2004/0233059 A1 | 11/2004 | Smith et al. |
| 2009/0160643 A1 | 6/2009 | Lizza |
| 2009/0227223 A1 | 9/2009 | Jenkins |
| 2011/0260873 A1 * | 10/2011 | Ouchi ................. G08B 25/016 |
| | | 340/573.3 |
| 2012/0312247 A1 | 12/2012 | Ebersole |
| 2013/0104812 A1 | 5/2013 | Levi et al. |
| 2016/0302390 A1 | 10/2016 | Allen |
| 2016/0316716 A1 | 11/2016 | Hanson |
| 2016/0337618 A1 | 11/2016 | Chapman et al. |
| 2017/0238506 A1 | 8/2017 | Swartz |
| 2018/0012477 A1 | 1/2018 | Lewis |
| 2018/0014506 A1 | 1/2018 | Foster et al. |
| 2018/0151047 A1 | 5/2018 | Brunner et al. |
| 2018/0199546 A1 | 7/2018 | Temel |
| 2018/0303064 A1 | 10/2018 | Nowling |
| 2019/0068850 A1 | 2/2019 | Peper, Jr. et al. |

OTHER PUBLICATIONS

Grace, Kea, "Service Dog FIDO Vest: Wearable Technology for Working Dogs", Gear and Equipment, Dated: Jan. 20, 2015, 4 pages.

"Apple Inc., Use Emergency SOS on your iPhone—Apple Support", Dated: 2020, 5 pages.

* cited by examiner

FIG. 6
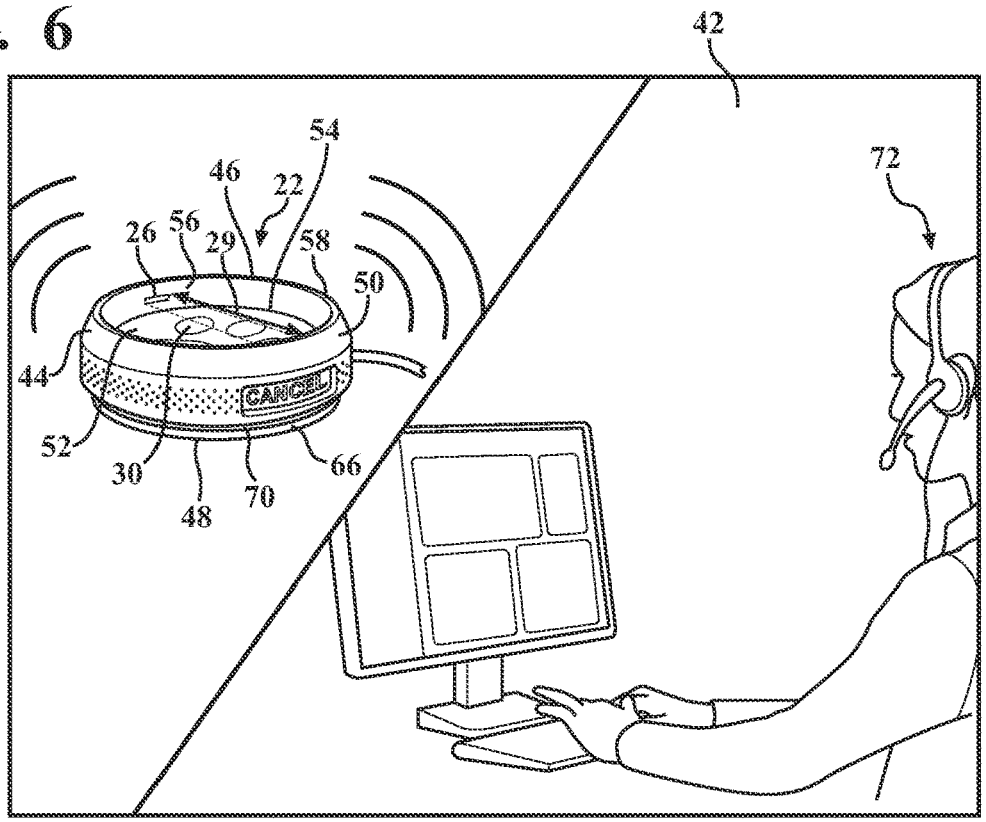
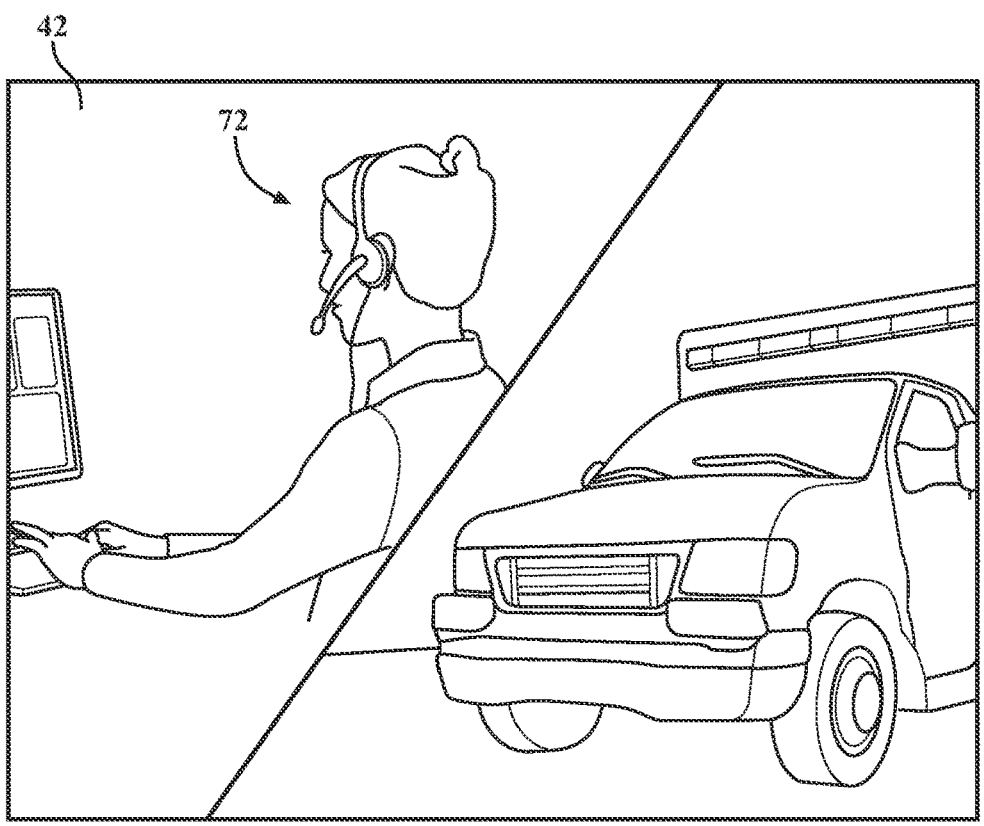
FIG. 7

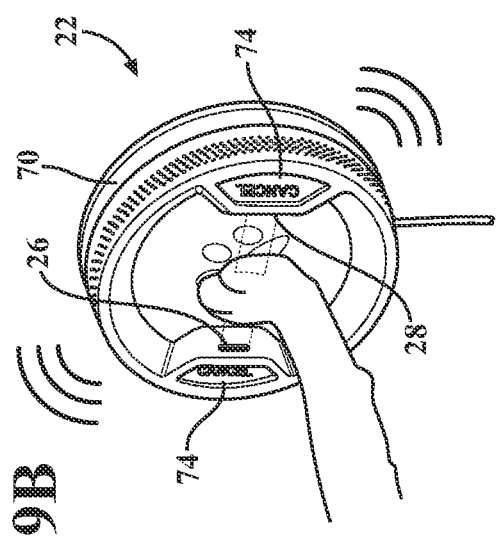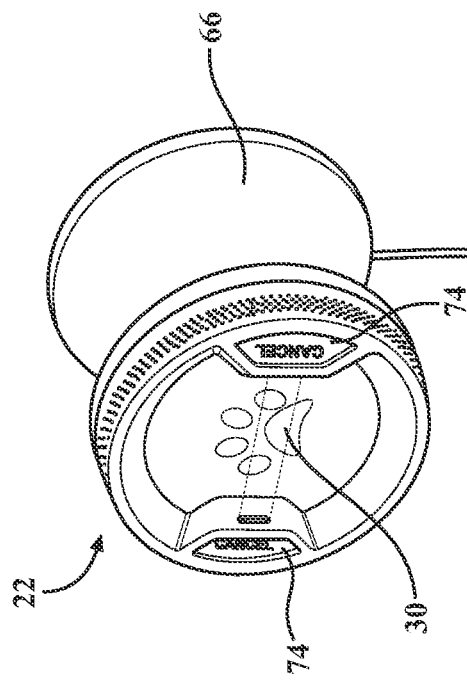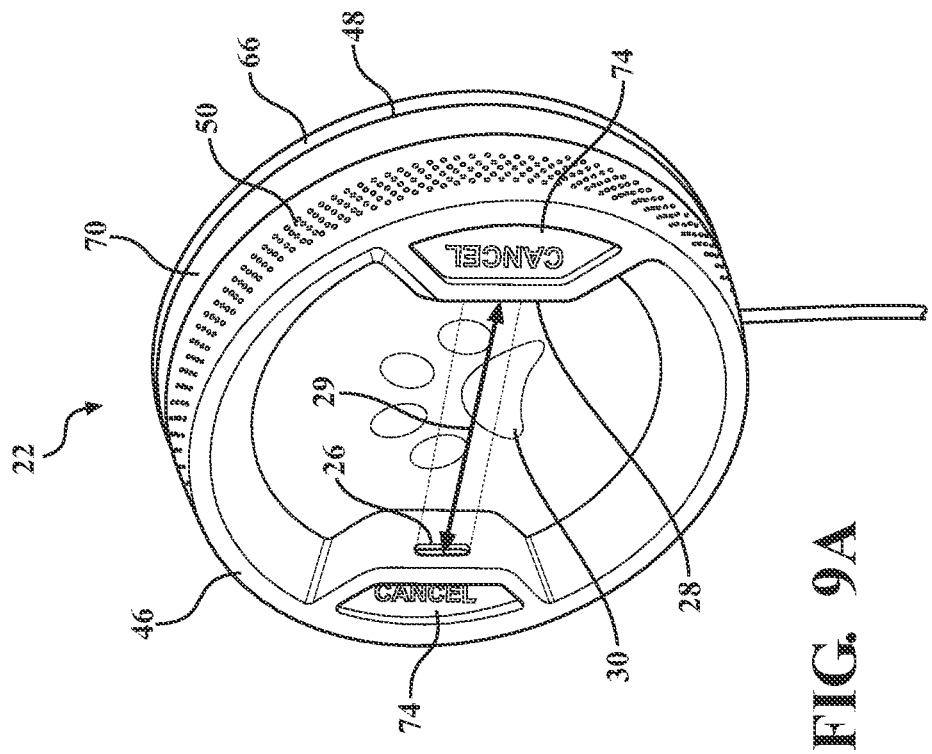

FIG. 15
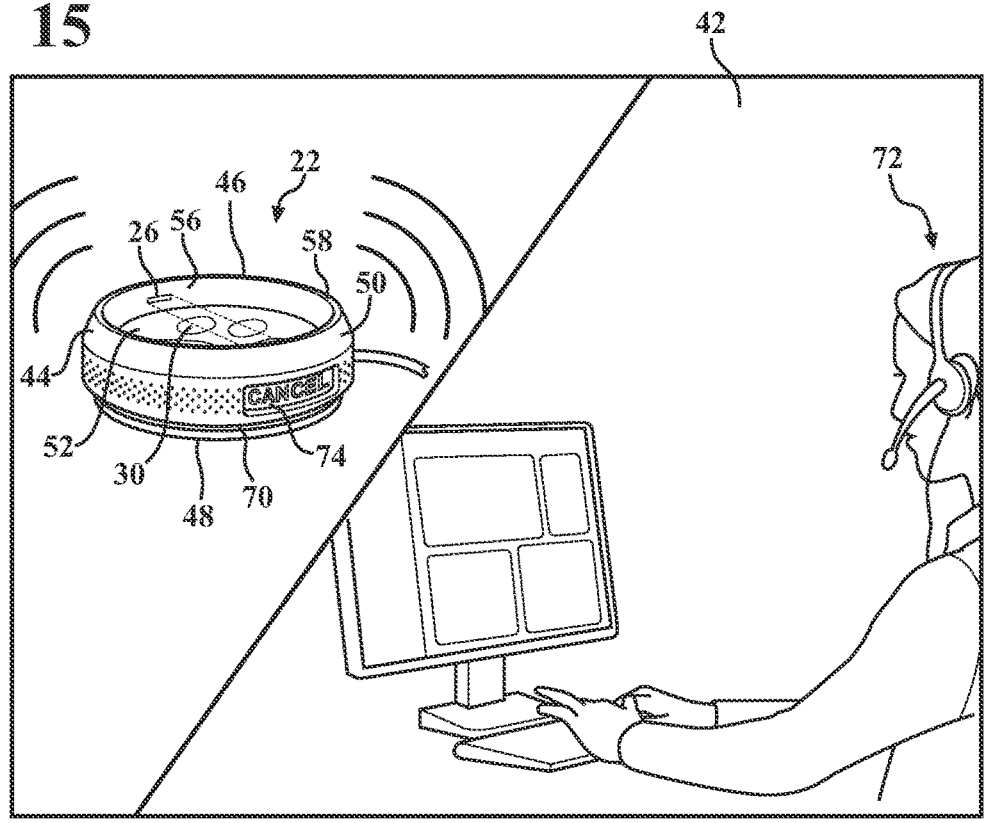
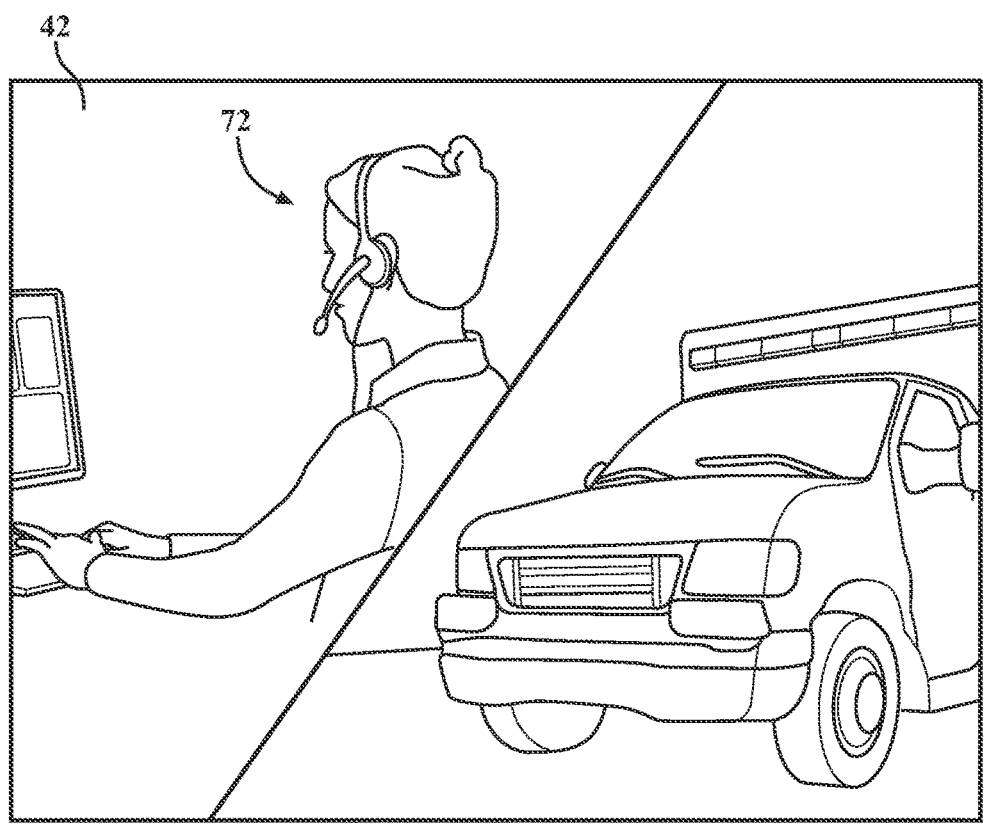
FIG. 16

FIG. 20
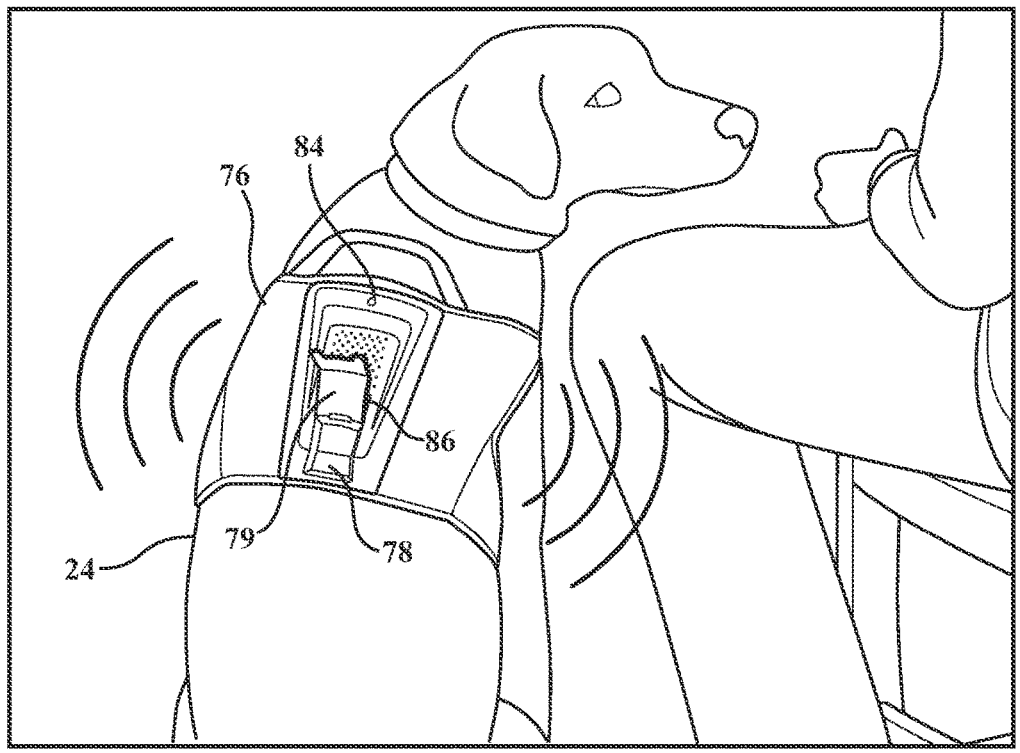
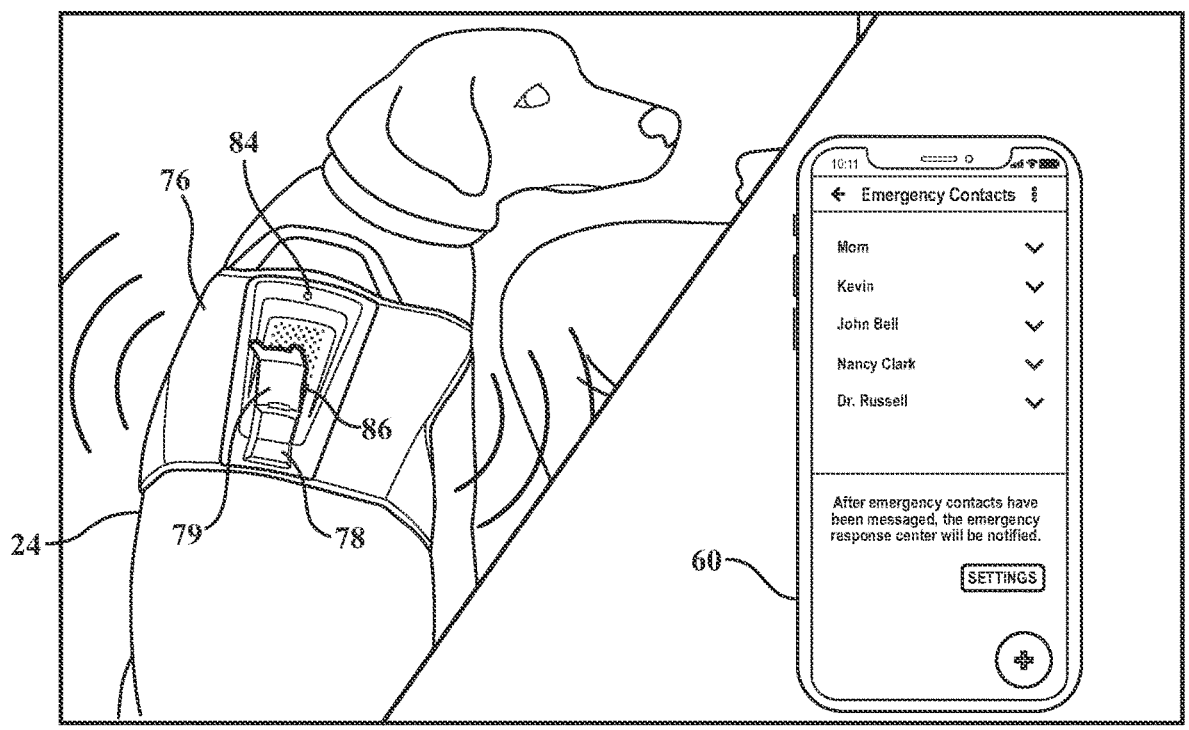
FIG. 21

FIG. 22
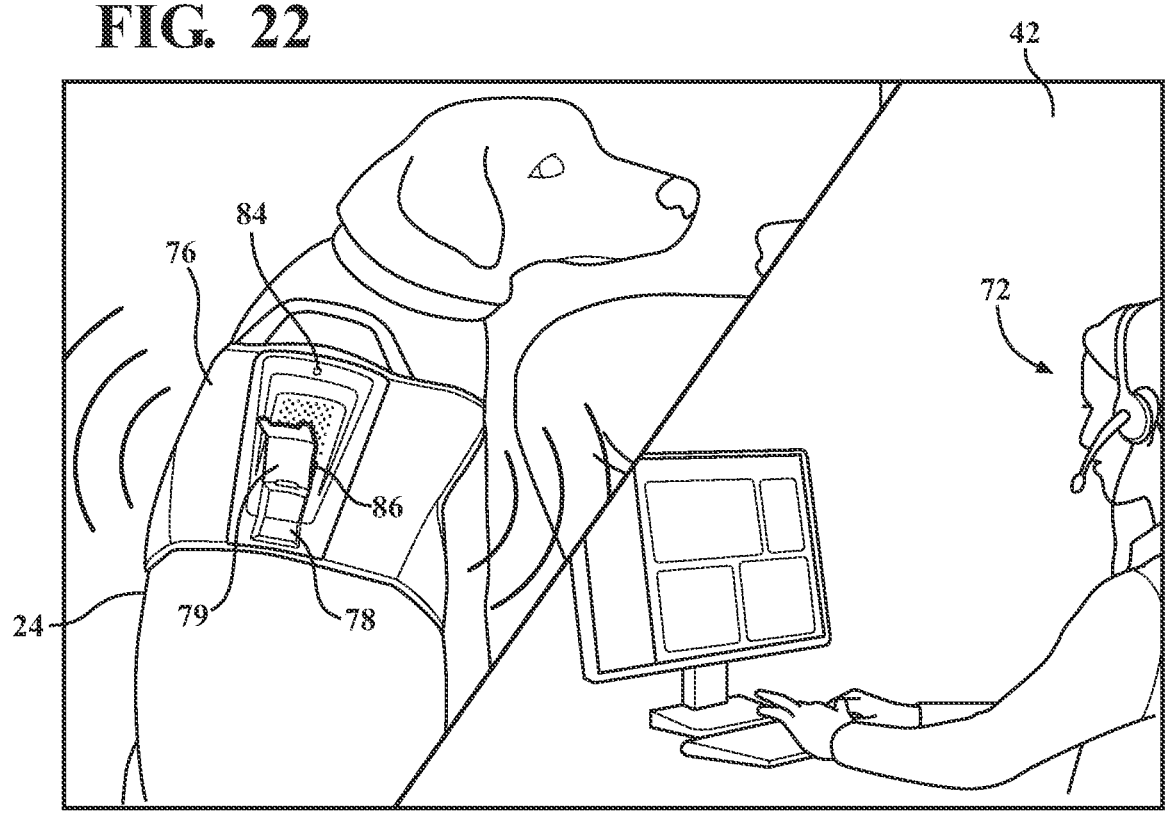
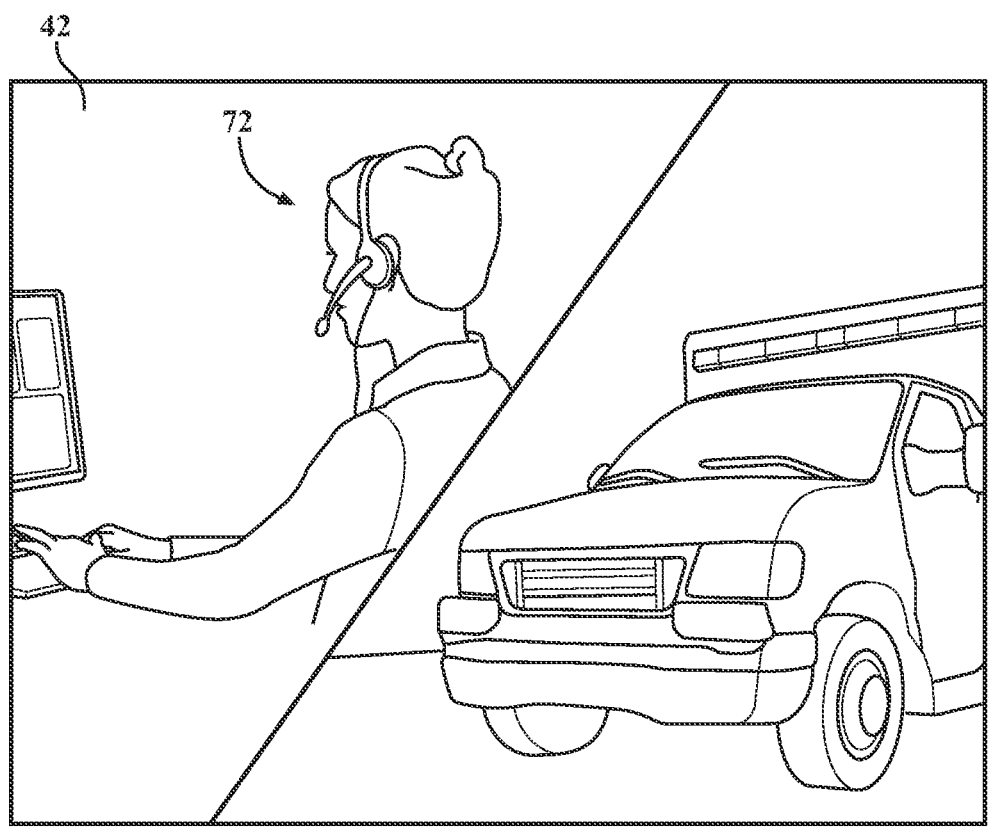
FIG. 23

CANINE EMERGENCY ALERT SYSTEM

CROSS-REFERENCE TO RELATED APPLICATION

This utility application claims the benefit of U.S. Provisional Application No. 63/006,183 filed Apr. 7, 2020 titled "Canine Emergency Alert System". The provisional application is incorporated by reference herein as if reproduced in full below.

FIELD

The present disclosure relates generally to emergency alert systems. More particularly, the present disclosure is directed to an emergency alert system involving service canines.

BACKGROUND

This section provides background information related to the present disclosure which is not necessarily prior art.

Service animals, such as canines, may be trained to assist people with various tasks. According to at least one source, there are currently over 500,000 service dogs working in the United States. Such service animals can be trained to recognize situations in which an owner of the service animal may become incapacitated or otherwise unable to request assistance (e.g., in the event of a medical emergency). In such situations, it may be necessary for the service animal to summon help.

Known emergency alert systems intended to be actuated by service animals include modified versions of medical alert systems originally designed solely for human actuation (e.g., Life Alert®). While such modified human-actuated systems may be capable of notifying medical professionals and/or family members once they are actuated, successful actuation by the service animal during the medical emergency remains challenging. More specifically, known human-actuated emergency alert systems rely on actuation of a push button or momentary switch. Consequently, modified human-actuated systems typically involve some sort of additional outer housing or mechanism that enables the service animal to push the existing push button or momentary switch with their nose or a limb (e.g., if mounted on the wall or floor). However, as such modified human-actuated systems require precise mechanical actuation of the push button or momentary switch, training the service animal to reliably activate the system and subsequent operation by the service animal when needed remains difficult. Such precise mechanical actuation by service animals is further exacerbated because service animals may not always perform well under stress (especially in a noisy public setting). Thus, in the event of a medical emergency, the service animal may not consistently operate the modified push button or momentary switch successfully, for example.

In addition, as such modified human-actuated systems were originally designed for use by humans, any interactive notification features (e.g., audible alerts) are exclusively intended for humans, not service animals. Thus, such interactive notification features may not always effectively communicate to the service animal that the system is notifying medical professionals and/or family members of the medical emergency, for example. Similarly, the notification features of such modified human-actuated systems or other known emergency alert systems may not be conducive to successful training of the service animal to use.

Furthermore, known emergency alert systems do not effectively utilize available modern location and communication technology. Therefore, the operation may be limited, especially when such emergency alert systems are operated in a portable context.

Thus, there remains a need to develop alternative emergency alert apparatuses and systems that may be more easily actuated by service animals and provide enhanced operational capabilities.

SUMMARY

This section provides a general summary of the present disclosure and is not a comprehensive disclosure of its full scope or all of its features, aspects and objectives.

It is an aspect of the present disclosure to provide an emergency alert pad operable by a service animal. The pad includes an optical transmitter facing a first direction for transmitting a light beam in the first direction. An optical receiver is spaced from the optical transmitter by a transmission spacing to define an air gap sized to receive an appendage of the service animal and facing a second direction opposite the first direction for receiving the light beam from the optical transmitter transmitted across the air gap. The pad also includes a pad communications transceiver for communicating a pad alert and a pad control unit coupled to the optical transmitter and the optical receiver and the pad communications transceiver. The pad control unit is configured to communicate the pad alert using the pad communications transceiver in response to the optical receiver detecting that the light beam has been obstructed by the appendage of the service animal.

In accordance with another aspect, there is provided an emergency alert system. The system includes an emergency alert pad configured to detect a pad activation by a service animal and communicate a pad alert in response to detecting the pad activation by the service animal. The system also includes an emergency alert vest worn by the service animal and configured to detect a vest activation by a person in proximity to the service animal and communicate a vest alert in response to detecting the vest activation by the person in proximity to the service animal. A user mobile device is in communication with the emergency alert pad and the emergency alert vest and configured to record a pre-recorded message stored by the emergency alert pad and the emergency alert vest. At least one affiliated mobile device is also in communication with the emergency alert pad and the emergency alert vest. The at least one affiliated mobile device is configured to receive the pre-recorded message from the emergency alert pad during the pad activation and from the emergency alert vest during the vest activation. In addition, an emergency response center is in communication with the emergency alert pad and the emergency alert vest and is configured to receive at least one of the pad alert and the vest alert and provide emergency services in response to receiving at least one of the pad alert and the vest alert.

In accordance with yet another aspect of the disclosure, a method of operating an emergency alert system including an emergency alert pad operable by a service animal is provided. The method includes the step of transmitting a light beam in a first direction using an optical transmitter of the emergency alert pad facing the first direction. The method continues with the step of receiving the light beam from the optical transmitter transmitted across an air gap sized to receive an appendage of the service animal using an optical receiver of the emergency alert pad spaced from the optical transmitter by a transmission spacing and facing a second direction opposite the first direction. The method continues by detecting a pad activation by the service animal. Specifically, the pad activation includes the light beam being obstructed by the appendage of the service animal and detected by the optical receiver. The method also includes the step of communicating a pad alert using a pad communications transceiver of the emergency alert pad in response to detecting the pad activation.

In accordance with another aspect, there is provided another method of operating an emergency alert system. The method includes the step of recording a pre-recorded message using a user mobile device. The method continues with the step of storing the pre-recorded message on an emergency alert pad and an emergency alert vest in communication with the user mobile device. The next step of the method is detecting a pad activation by a service animal and communicating a pad alert in response to detecting the pad activation by the service animal using the at least one emergency alert pad. The method also includes the step of detecting a vest activation by a person in proximity to the service animal and communicating a vest alert in response to detecting the vest activation by the person in proximity to the service animal using the emergency alert vest. The method proceeds by receiving the pre-recorded message from the emergency alert pad during a pad activation and from the emergency alert vest during a vest activation using at least one affiliated mobile device in communication with the emergency alert pad and the emergency alert vest. Next, receiving at least one of the pad alert and the vest alert and providing emergency services in response to receiving the at least one of the pad alert and the vest alert using an emergency response center in communication with the emergency alert pad and the emergency alert vest.

The emergency alert pad, system, and method can therefore provide improved operational capabilities when operated by service animals and/or humans. Improved training effectiveness and increased probability of successful actuation by the service animal to request assistance are also enabled.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 2-9C illustrate an emergency alert pad of the emergency alert system of FIG. 1 used in a home according to aspects of the disclosure;

FIGS. 10-17 illustrate the emergency alert pad of the emergency alert system of FIG. 1 being portable according to aspects of the disclosure;

FIGS. 18-24 illustrate an emergency alert vest of the emergency alert system of FIG. 1 worn by a service animal according to aspects of the disclosure;

DETAILED DESCRIPTION

In the following description, details are set forth to provide an understanding of the present disclosure. In some instances, certain circuits, structures and techniques have not been described or shown in detail in order not to obscure the disclosure.

In general, example embodiments of an emergency alert system constructed in accordance with the teachings of the present disclosure will now be disclosed. The example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are described in detail.

Figure 1:
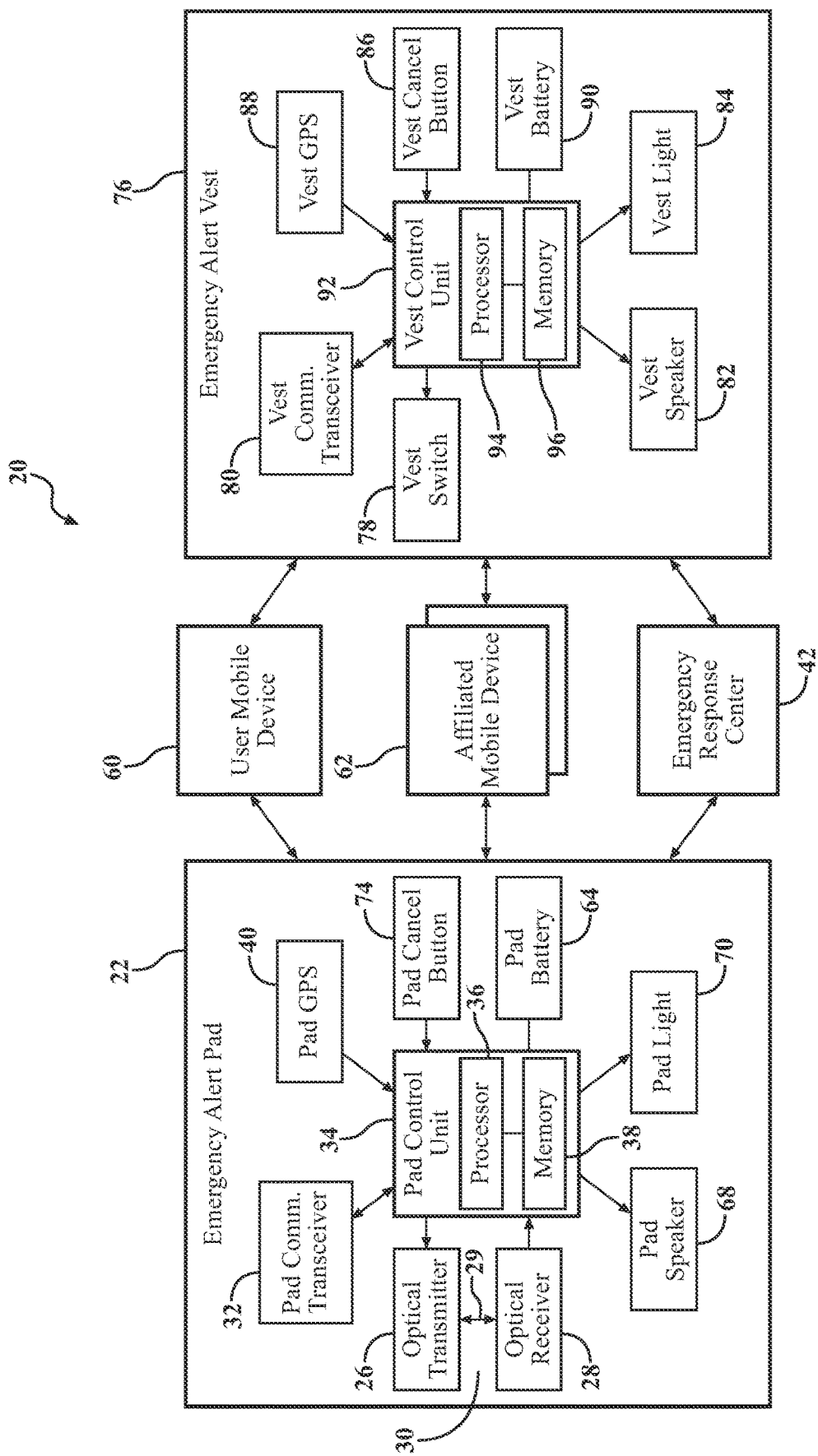
FIG. 1 is a block diagram of an emergency alert system according to aspects of the disclosure.

Referring initially to FIG. 1, an exemplary emergency alert system 20 is shown. The system 20 includes an emergency alert pad 22 configured to detect a pad activation by a service animal 24 (e.g., a canine) and communicate a pad alert in response to detecting the pad activation by the service animal 24. As shown in FIG. 1 and also referring to FIGS. 2-9, the emergency alert pad 22 includes an optical transmitter 26 facing a first direction for transmitting a light beam (e.g., infrared) in the first direction. An optical receiver 28 is spaced from the optical transmitter 26 by a transmission spacing 29 to define an air gap 30 sized to receive an appendage of the service animal 24 (e.g., the paw or nose of the service animal 24). The optical receiver 28 faces a second direction opposite the first direction for receiving the light beam from the optical transmitter 26 transmitted across the air gap 30. The emergency alert pad 22 also includes a pad communications transceiver 32 for communicating the pad alert (e.g., via Bluetooth, WIFI, Global System for Mobile Communications/GSM, Code-Division Multiple Access/CDMA, Long-Term Evolution (LTE), and/or hard-wire phone capability) and a pad control unit 34 coupled to the optical transmitter 26 and the optical receiver 28 and the pad communications transceiver 32. The pad control unit 34 is configured to communicate the pad alert using the pad communications transceiver 32 in response to the optical receiver 28 detecting that the light beam has been obstructed by the appendage of the service animal 24. The pad control unit 34 includes a pad processor 36 (e.g., a microprocessor or microcontroller) and a pad memory 38 in communication with the pad processor 36. The pad memory 38 can, for example, include instructions (i.e., software) executed by the pad processor 36 to carry out the functions described herein.

The emergency alert pad 22 also includes a pad global positioning system (GPS) receiver 40 coupled to the pad control unit 34 for ascertaining a geographical location of the emergency alert pad 22. Using the pad global positioning system receiver 40, the pad control unit 34 is configured to determine the geographical location of the emergency alert pad 22. The pad control unit 34 is also configured to transmit the geographical location of the emergency alert pad 22 to an emergency response center 42 using the pad communications transceiver 32 in response to the optical receiver 28 detecting that the light beam has been obstructed by the appendage of the service animal 24.

The emergency alert pad 22 includes a pad housing 44 that is cylindrically shaped and has a top 46 and a bottom 48. The pad housing 44 also includes a peripheral wall 50 extending circumferentially around and between the top 46 and the bottom 48. The top 46 includes a recessed platform 52 that is circular and parallel to and spaced from the bottom 48 to define a recess 54 that extends into the pad housing 44 toward the bottom 48 a recess depth and an inner lip 56 extending circumferentially around the recessed platform 52. The inner lip 56 also extends from the recessed platform 52 to the peripheral wall 50 at a rim 58. The optical transmitter 26 is disposed on the inner lip 56 and is configured to transmit the light beam along the recessed platform 52 across the recess 54 (i.e., across the air gap 30). Similarly, the optical receiver 28 is disposed on the inner lip 56 and is circumferentially spaced from the optical transmitter 26 by approximately 180 degrees and is configured to receive the light beam from the optical transmitter 26. The pad housing 44 enables the emergency alert pad 22 to be placed on a floor or mounted on a wall (FIGS. 9A-9C). While the optical transmitter 26 and optical receiver 28 are shown directly opposite one another across the air gap 30 in the cylindrically shaped pad housing 44, it should be appreciated that other types of housings and arrangements of the optical transmitter 26 and optical receiver 28 are contemplated.

The pad communications transceiver 32 of the emergency alert pad 22 is in communication with at least one mobile device 60, 62 (e.g., a user mobile device 60). In addition, the pad control unit 34 is configured to store the pre-recorded message recorded by the at least one mobile device 60, 62 in the pad memory 38. The emergency alert pad 22 also can include a pad battery 64 (e.g., lithium ion or other rechargeable battery) coupled to the pad control unit 34 for storing electrical energy used by the emergency alert pad 22.

Figure 2:
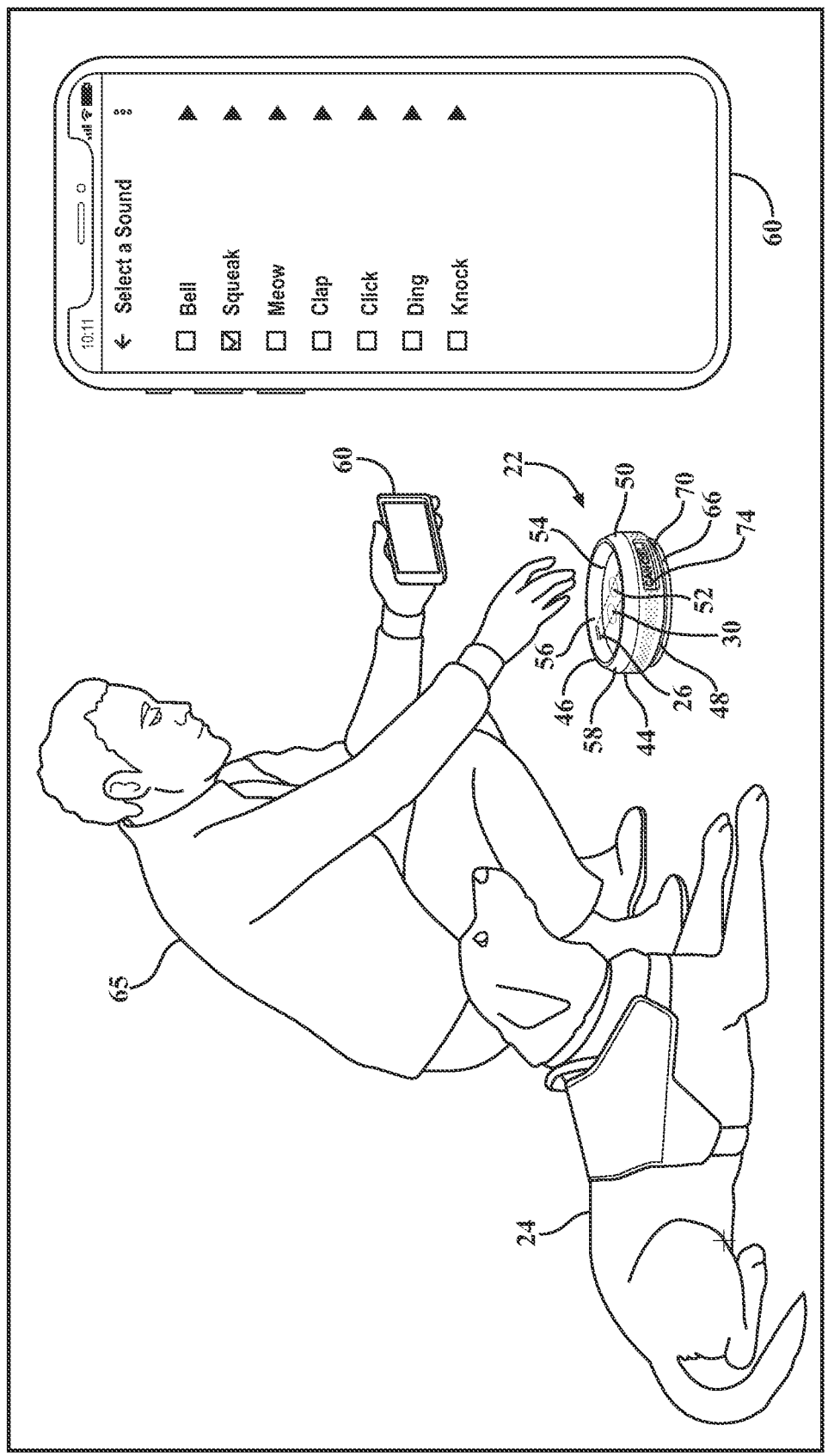

As best shown in FIG. 2, the emergency alert pad 22 can dock with or rest on top of a docking pad 66 to recharge the pad battery 64 (e.g., via a wired connector (not shown) or inductive wireless charging). The emergency alert pad 22 additionally includes a pad speaker 68 (FIG. 1) coupled to the pad control unit 34 for emitting an audible pad feedback sound. The emergency alert pad 22 also includes a pad light 70 for emitting a visible pad notification light (e.g., flashing).

Still referring to FIG. 2, the user mobile device 60 is in communication with the emergency alert pad 22 and is configured to record a pre-recorded message stored by the at least one emergency alert pad 22. Nevertheless, the pre-recorded message could be stored elsewhere instead (e.g., at a cloud services provider or at the emergency response center 42). Thus, an owner 65 of the service animal 24 sets up the emergency alert pad 22 (e.g., plugs into the charging dock 66 or rests on top of the charging dock 66 to charge the pad battery 64) and selects the audible pad feedback sound best suited to their service animal 24 (e.g., service dog's favorite sound, to ensure that the service dog is getting his or her "favorite" sound for a reward) with a mobile application operated on the at least one mobile device 60, 62 (e.g., the user mobile device 60). The mobile application operated on the user mobile device 60 not only allows the selection of the audible pad feedback sound (e.g., chime, squeak, bell, etc.), but provides monitoring of the pad battery 64 with an alert when the pad battery 64 gets below a predetermined charge level (e.g., 30%). In addition, the mobile application provides an ability to input specific phone numbers that the emergency alert pad 22 will call in the event of an emergency. Others besides the owner 65 (e.g., family members of the owner 65) may also download the mobile application onto at least one affiliated mobile device 62 (e.g., a mobile phone operated by a family member of the owner 65 of the service animal 24) and update settings for the emergency alert pad 22, for example.

Figure 3:
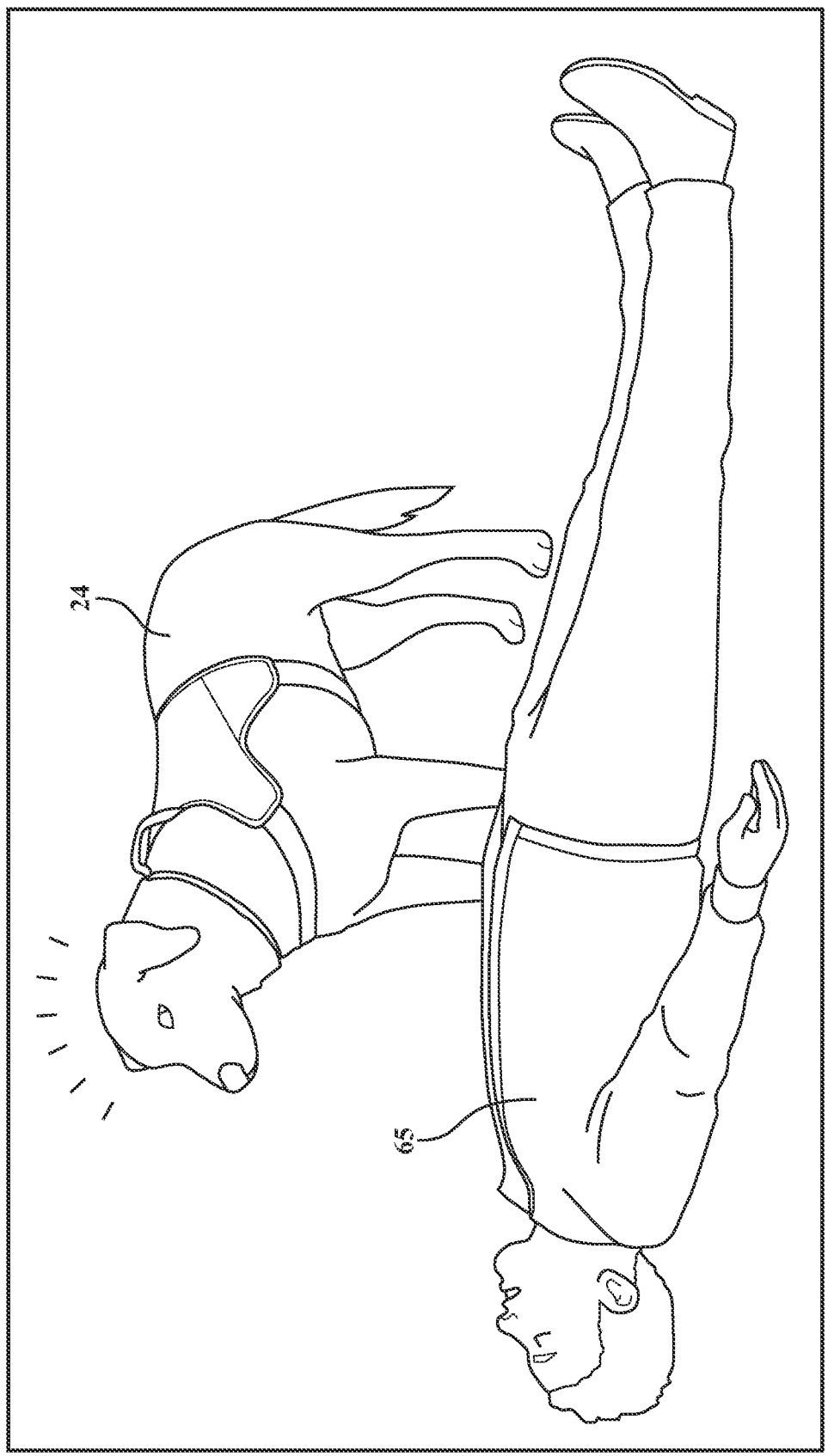
Figure 4:
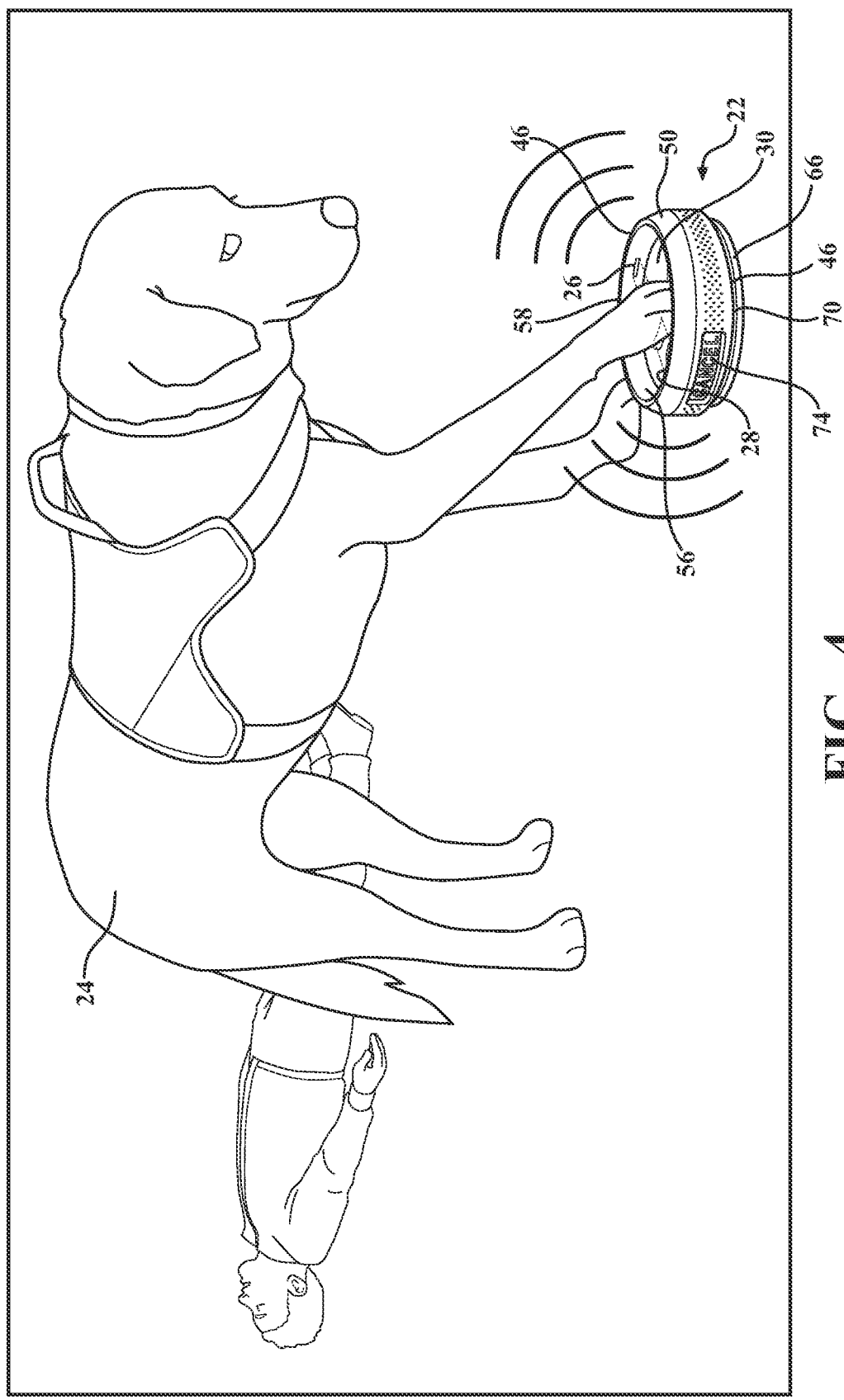

As shown in FIG. 3, after setup of the emergency alert pad 22, the service animal 24 is alerted, because of its training, when the owner 65 begins having a medical emergency. So, as best shown in FIG. 4, the service animal 24 then goes to the emergency alert pad 22 and quickly swipes at the optical sensor of the emergency alert pad 22 (i.e., the optical transmitter 26 and optical receiver 28) interrupting the light beam. The emergency alert pad 22 then plays the audible pad feedback sound and begins flashing the pad light 70. So, the pad control unit 34 is further configured to produce the audible pad feedback sound using the pad speaker 68 and the visible pad notification light using the pad light 70 in response to the optical receiver 28 detecting that the light beam has been obstructed by the appendage of the service animal 24 (e.g., the paw or nose of the service animal 24).

Figure 5:
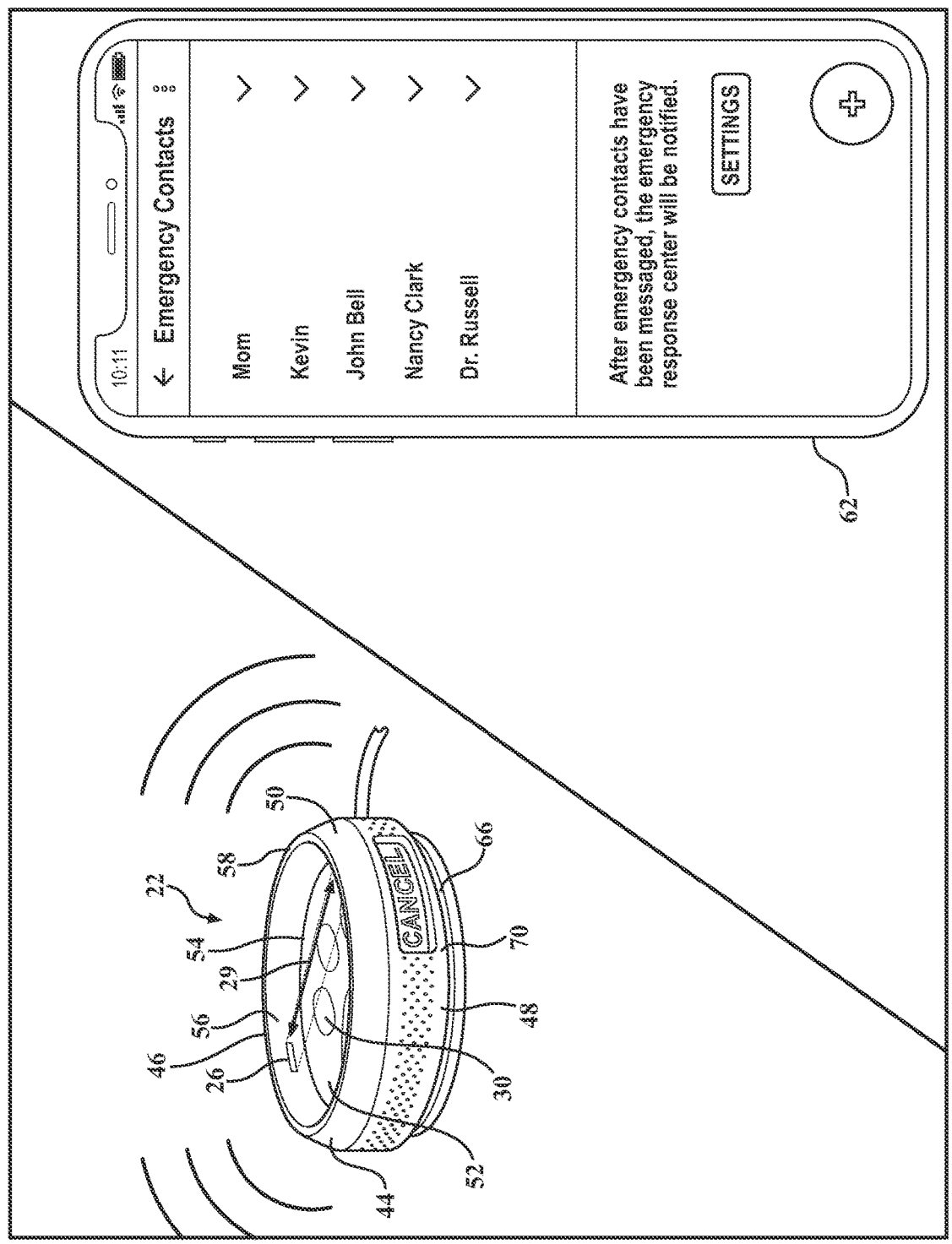

Referring back to FIG. 1, the at least one affiliated mobile device 62 is also in communication with the at least one emergency alert pad 22. As shown in FIG. 5, after being activated, the emergency alert pad 22 dials or otherwise alerts emergency contacts with the pre-recorded message. Specifically, the pad control unit 34 is also configured to transmit the pre-recorded message to a plurality of emergency contacts and the at least one affiliated mobile device 62 is configured to receive the pre-recorded message from the emergency alert pad 22 during the pad activation. While it is discussed above that the emergency alert pad 22 calls the emergency contacts to communicate the pre-recorded message, it should be understood that other means of communication may be used in addition to or in place of the phone calls to contact the emergency contacts (e.g., text messages, messages or notifications directly to the mobile application of the at least one affiliated mobile device 62). So, if the emergency alert pad 22 is activated by the service animal 24, anyone with the mobile application associated with a specific emergency alert pad 22 will be alerted on their at least one affiliated mobile device 62 along with a call and text, for instance.

As mentioned above, the emergency response center 42 is also in communication with the emergency alert pad 22 and is configured to receive the pad alert and provide emergency services in response to receiving the pad alert. So, as best shown in FIG. 6, the emergency alert pad 22 dials or otherwise contacts the emergency response center 42, which accesses the user's information and attempts to establish communication. A response agent 72 at the emergency response center 42 evaluates the situation involving the pad alert and decides if emergency services are needed. Thus, the pad control unit 34 is also configured to communicate the pad alert to the emergency response center 42 using the pad communications transceiver 32 in response to the optical receiver 28 detecting that the light beam has been obstructed by the appendage of the service animal 24. As shown in FIG. 7, if emergency services are needed, the response agent 72 contacts them and communicates the geographical location of the emergency alert pad 22 (e.g., ascertained by the pad GPS receiver 40) and medical information of the owner 65 (previously provided by the owner 65 or a family member, for example, using the mobile application).

Figure 8:
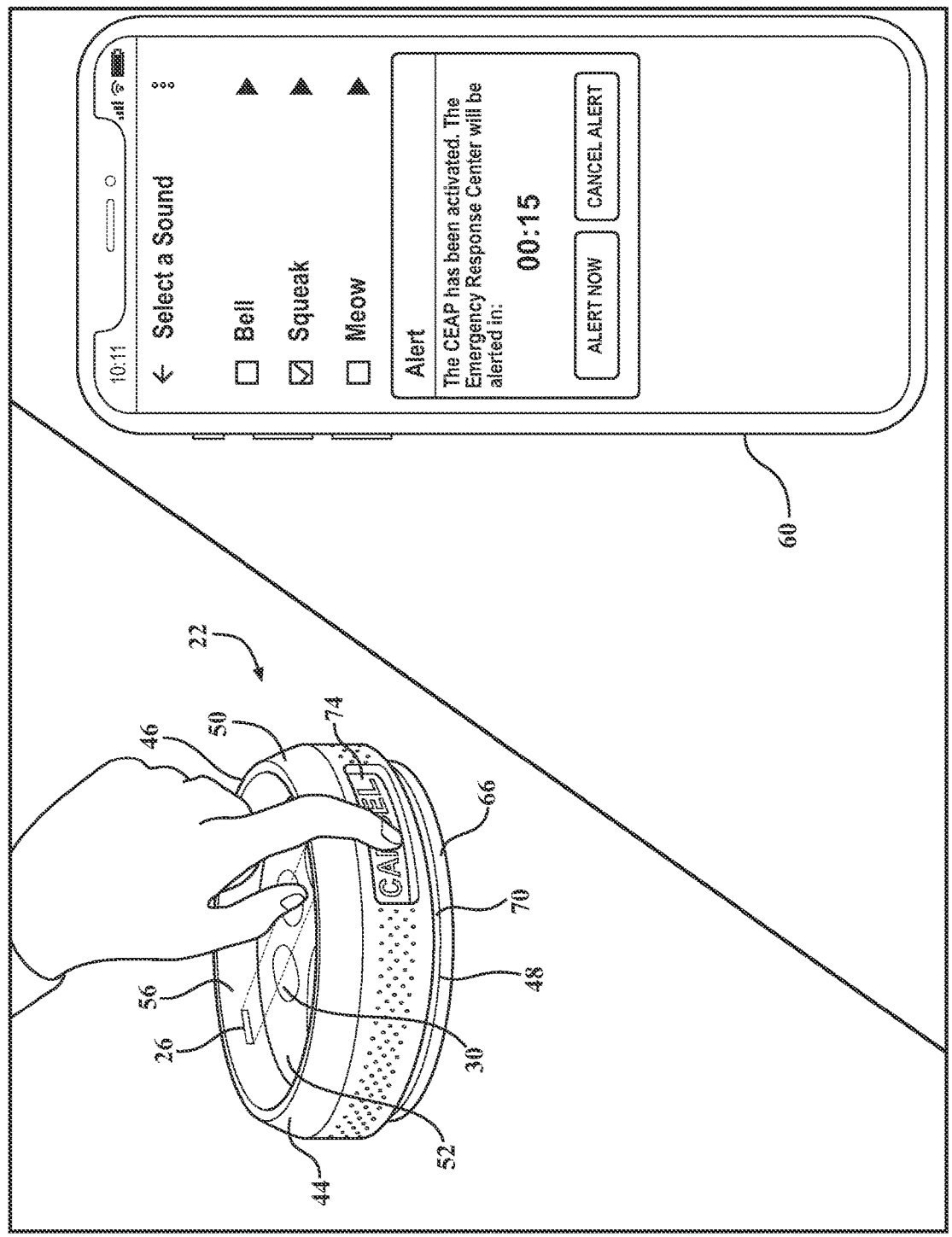

Referring now to FIG. 8, the emergency alert pad 22 also includes a pad cancel button 74 coupled to the pad control unit 34 and movable between a default pad position and a pad cancel alert position when activated. If the emergency alert pad 22 was mistakenly activated, the pad cancel button 74 (or a popup notification in the mobile application on the user mobile device 60) can be pushed to the pad cancel alert position to cancel the pad alert. Consequently, the pad control unit 34 is configured to cease communication of the pad alert in response to the pad cancel button 74 being moved to the pad cancel alert position. According to an aspect, the pad cancel button 74 is disposed on the peripheral wall 50; however, the pad cancel button 74 can alternatively be configured as shown in FIGS. 9A-9C on the top 46 of the emergency alert pad 22.

Figure 10:
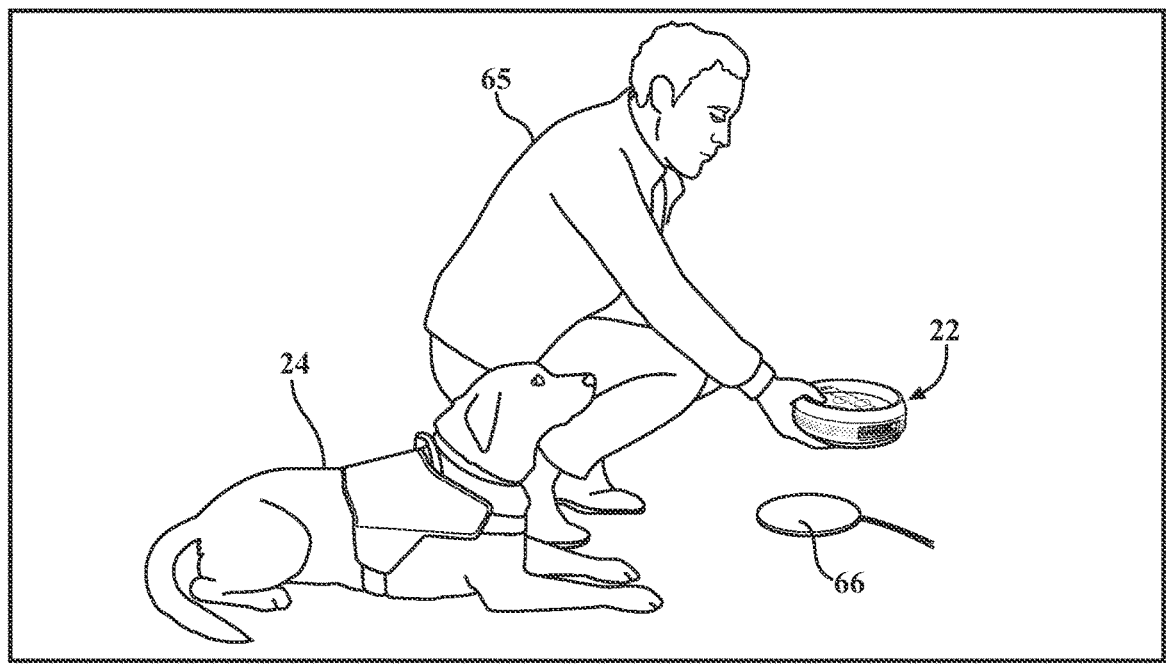
Figure 11:
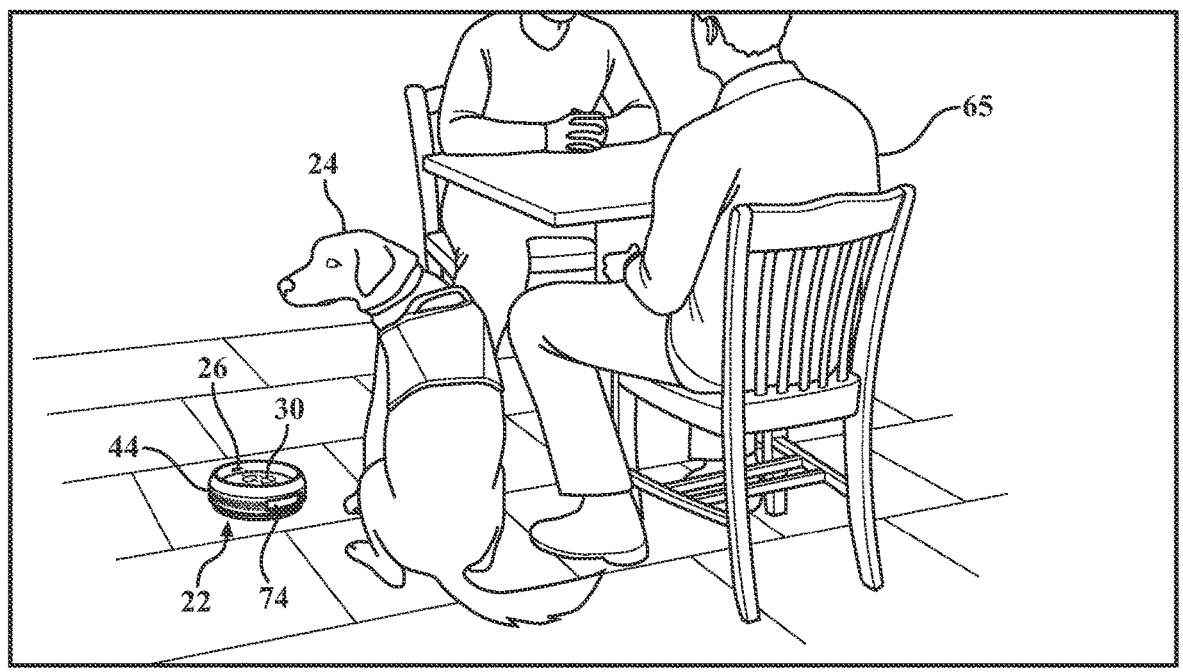
Figure 12:
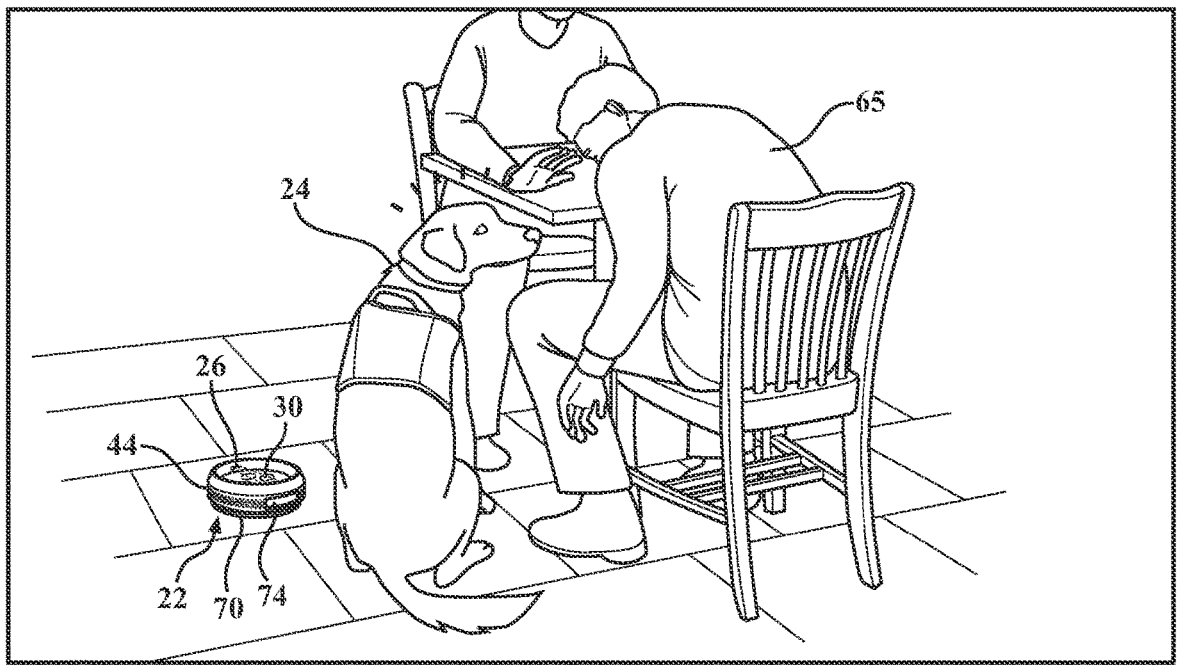
Figure 13:
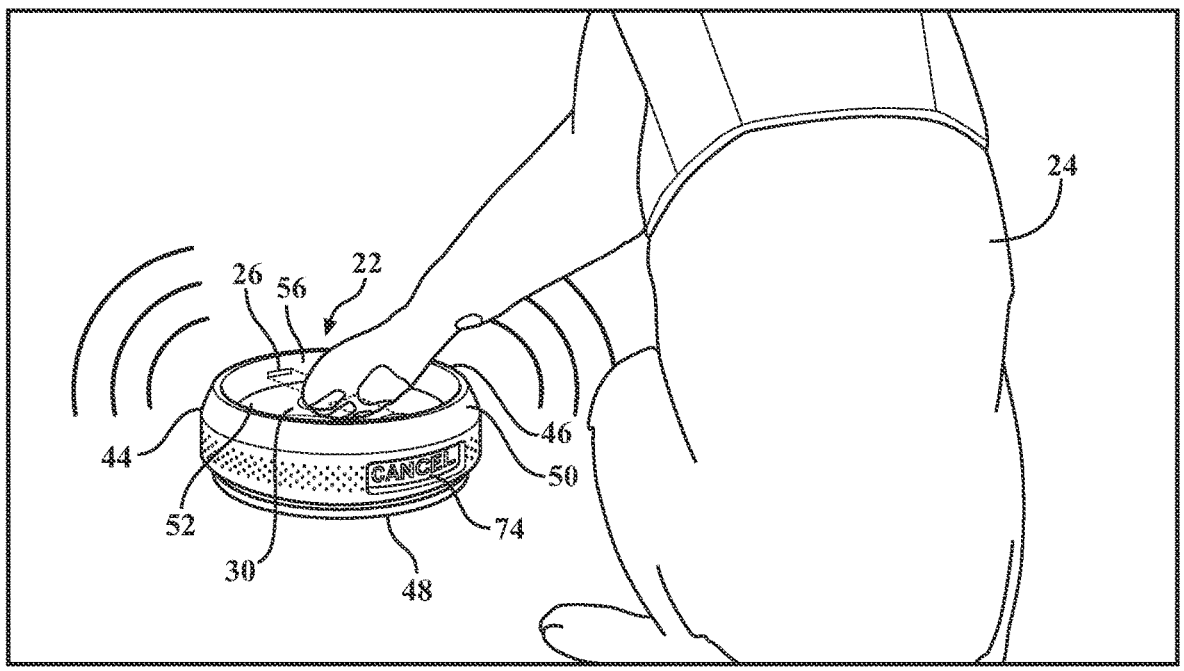

While the emergency alert pad 22 may be used within the confines of an owner's home, as best shown in FIGS. 10-17, the emergency alert pad 22 may also be portable and therefore used without wires in a home, or outside the owner's home. So, as shown in FIG. 10, the owner 65 of the service animal 24 can remove the emergency alert pad 22 (with a fully charged pad battery 64) from the charging dock 66 to take with them wherever they go. The owner 65 of the service animal 24 places the emergency alert pad 22 near themselves and their service animal 24, as shown in FIG. 11. Then, as best shown in FIG. 12, the service animal 24 is alerted because of its training when the owner 65 begins having a medical emergency. Next, in FIG. 13, the service animal 24 goes to the emergency alert pad 22 and quickly swipes through the light beam of the optical sensor to activate the emergency alert pad 22. The emergency alert pad 22 plays the audible pad feedback sound using the pad speaker 68 (rewarding the service animal 24 with their favorite sound) and begins flashing the pad light 70.

Figure 14:
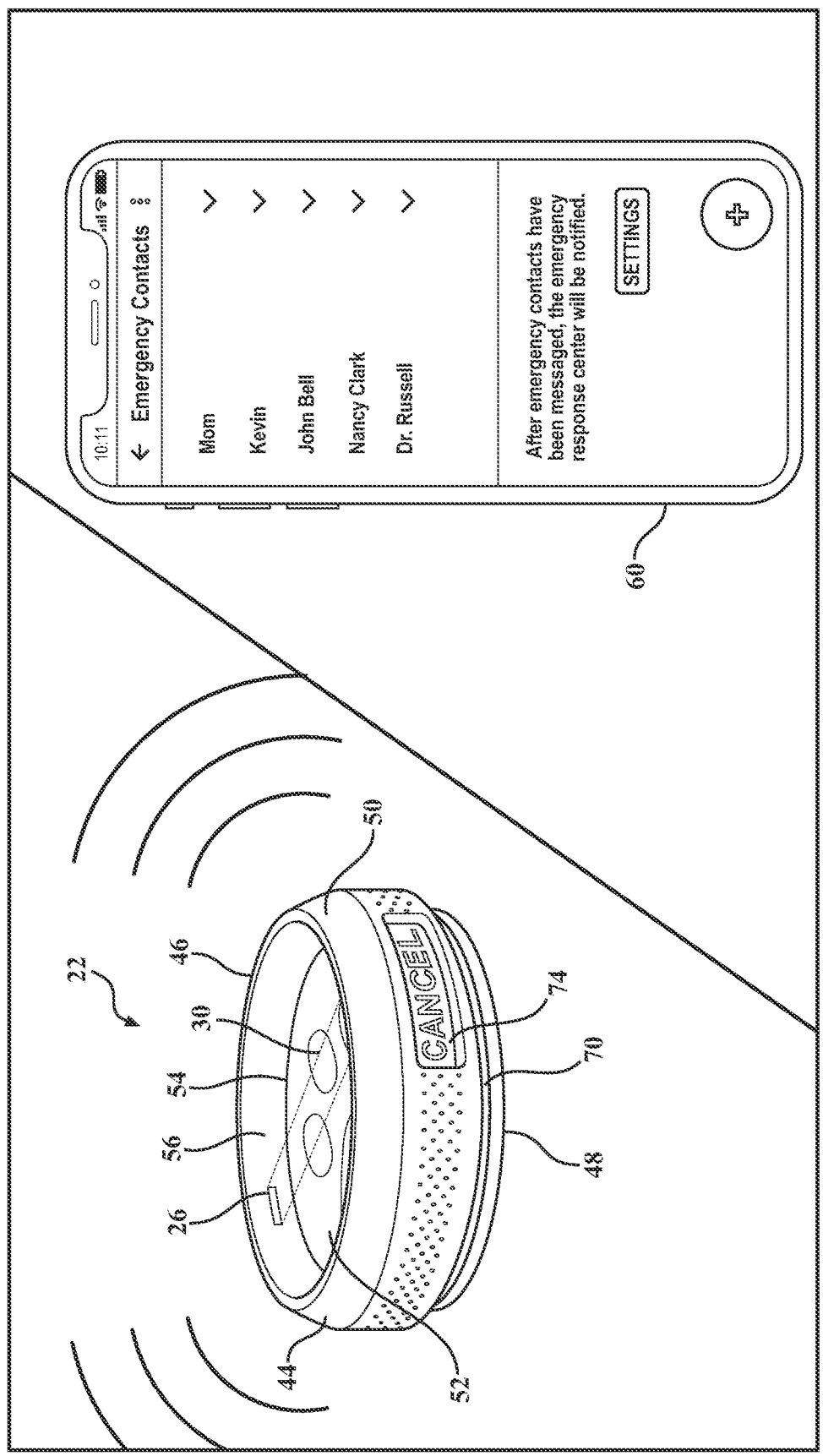
Figure 17:
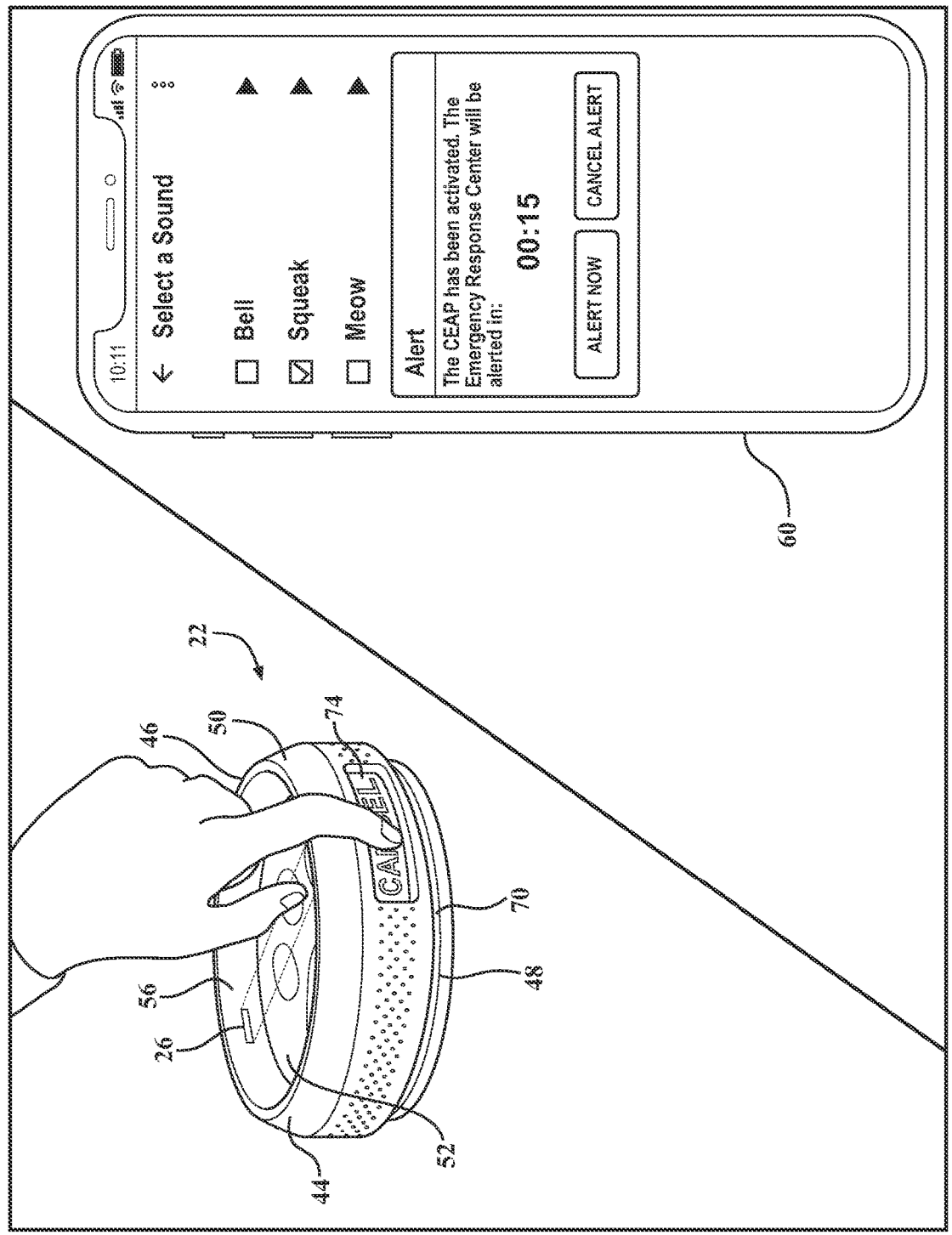

Referring to FIG. 14, after being activated, the emergency alert pad 22 dials and alerts or otherwise contacts the emergency contacts with the pre-recorded message (e.g., via the at least one affiliated mobile device 62). As best shown in FIG. 15, the emergency alert pad 22 dials or otherwise contacts the emergency response center 42, which accesses the user's information and attempts to establish communication. A response agent 72 of the emergency response center 42 evaluates the situation and decides if emergency services are needed. As shown in FIG. 16, if emergency services are needed, the response agent 72 contacts them and communicates the geographical location of the emergency alert pad 22 (e.g., from the pad global positioning system receiver 40) and medical information of the owner 65. As shown in FIG. 17, if the emergency alert pad 22 was mistakenly activated, the pad cancel button 74 (or a popup notification in the mobile application on the user mobile device 60) can be pushed to cancel the pad alert.

Referring back to FIG. 1 along with FIGS. 18-24, the system 20 also includes an emergency alert vest 76 worn by the service animal 24 configured to detect a vest activation by a person in proximity to the service animal 24 (e.g., the owner 65 of the service animal 24 or another person nearby) and communicate a vest alert in response to detecting the vest activation by the person in proximity to the service animal 24. The emergency alert vest 76 includes a vest switch 78 movable between an inactivated vest position and an activated vest position when activated. The emergency alert vest 76 also includes a vest communications transceiver 80 for communicating the vest alert (e.g., via Bluetooth, WIFI, Global System for Mobile Communications/GSM, Code-Division Multiple Access/CDMA, and/or Long-Term Evolution/LTE), a vest speaker 82 for emitting an audible vest feedback sound, and a vest light 84 for emitting a visible vest notification light. Additionally, the emergency alert vest 76 includes a vest cancel button 86 movable between a default vest position and a vest cancel alert position when activated. The emergency alert vest 76 includes a vest global positioning system receiver 88 for ascertaining a geographical location of the emergency alert vest 76. The emergency alert vest 76 also includes a vest battery 90 (e.g., rechargeable) for powering the emergency alert vest 76.

Additionally, the emergency alert vest 76 includes a vest control unit 92 coupled to the vest switch 78 and the vest communications transceiver 80 and the vest speaker 82 and the vest light 84 and the vest cancel button 86 and the vest global positioning system receiver 88. The vest control unit 92 includes a vest processor 94 (e.g., a microprocessor or microcontroller) and a vest memory 96 in communication with the vest processor 94. The vest memory 96 can, for example, include instructions executed by the vest processor 94 to carry out the functions described herein.

The vest control unit 92 is configured to determine the geographical location of the emergency alert vest 76 using the vest global positioning system receiver 88. The vest control unit 92 communicates the vest alert and the geographical location of the emergency alert vest 76 to the emergency response center 42 using the vest communications transceiver 80 in response to the vest switch 78 being moved to the activated vest position. The vest control unit 92 also is configured to produce the vest feedback sound using the vest speaker 82 and the visible vest notification light using the vest light 84 in response to the vest switch 78 being moved to the activated vest position. In addition, the vest control unit 92 is configured to cease communication of the vest alert and stop producing the vest feedback sound and the visible vest notification light in response to the vest cancel button 86 being moved to the vest cancel alert position.

As with the emergency alert pad 22, the emergency response center 42 is also in communication with the emergency alert vest 76 and is configured to receive the vest alert and provide emergency services in response to receiving the vest alert. In addition, the user mobile device 60 is in communication with the emergency alert vest 76 and is configured to record the pre-recorded message stored by the emergency alert vest 76. Additionally, the at least one affiliated mobile device 62 (e.g., a mobile phone operated by a family member of the owner 65 of the service animal 24) is also in communication with the emergency alert vest 76. Like with the emergency alert pad 22, the at least one affiliated mobile device 62 is configured to receive the pre-recorded message or other communication from the emergency alert vest 76 during a vest activation. As with the emergency alert pad 22, it should be understood that the pre-recorded message could be stored elsewhere instead (e.g., at a cloud services provider or at the emergency response center 42).

Figure 18:
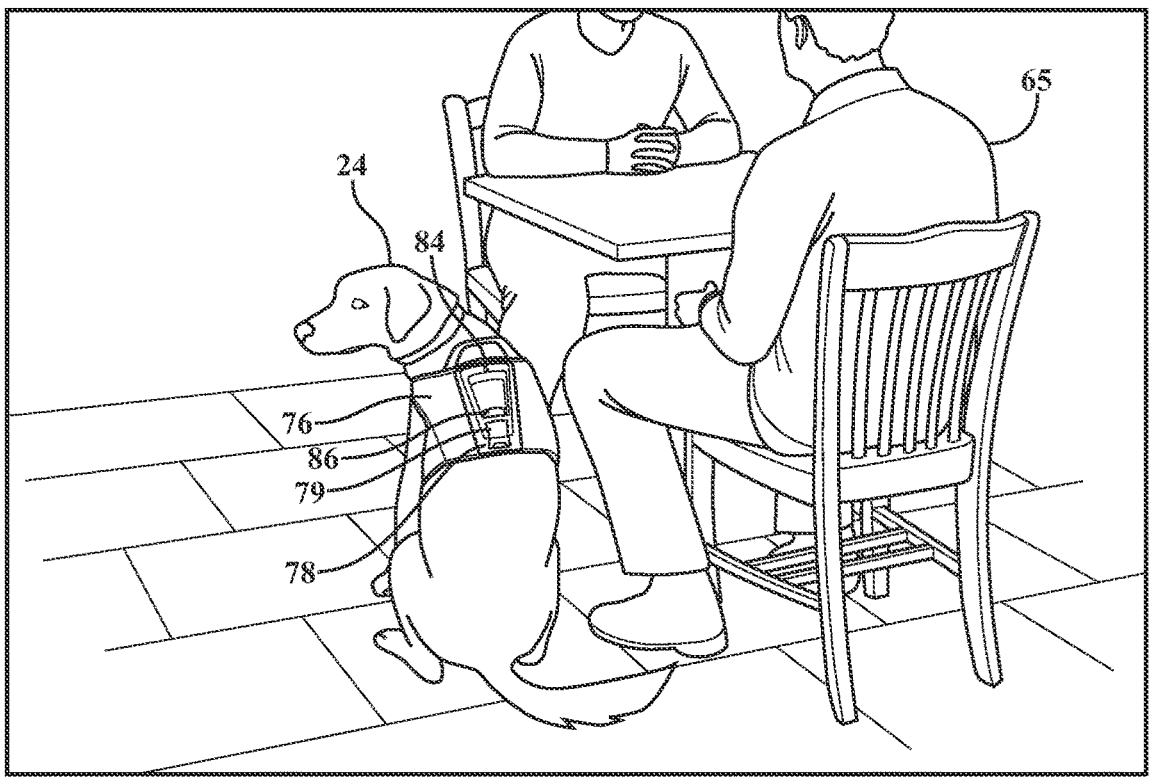
Figure 19:
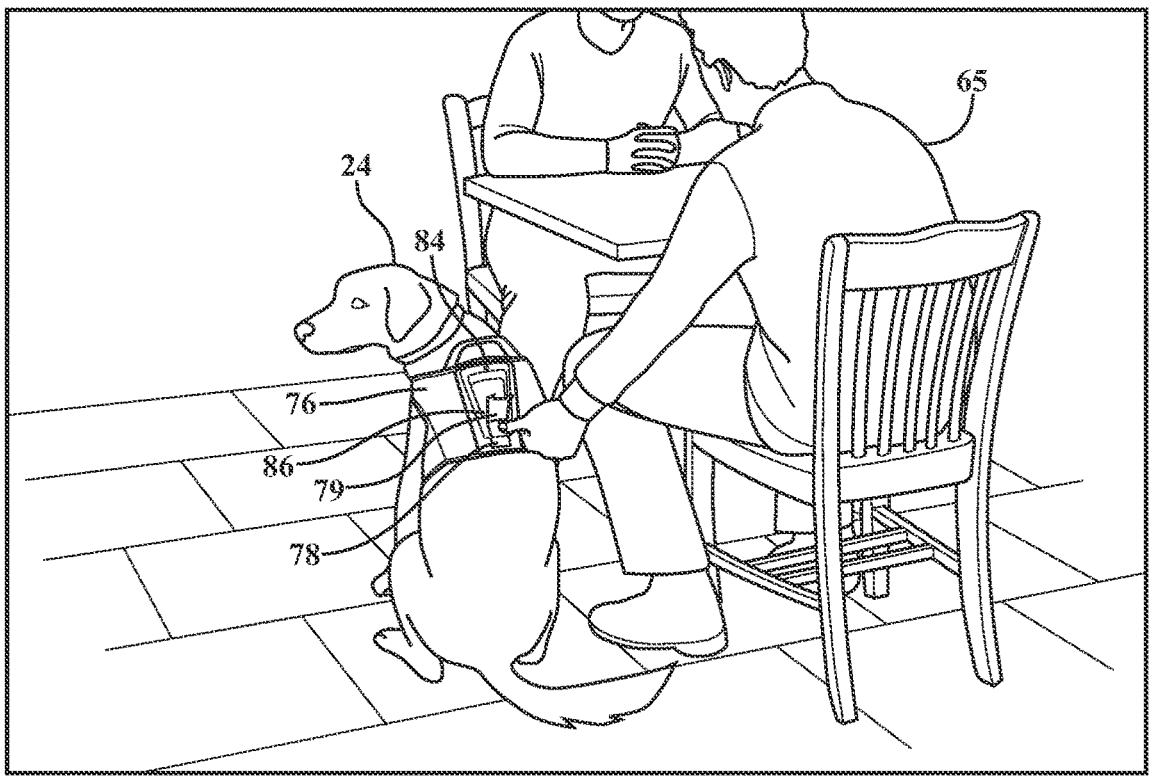
Figure 24:
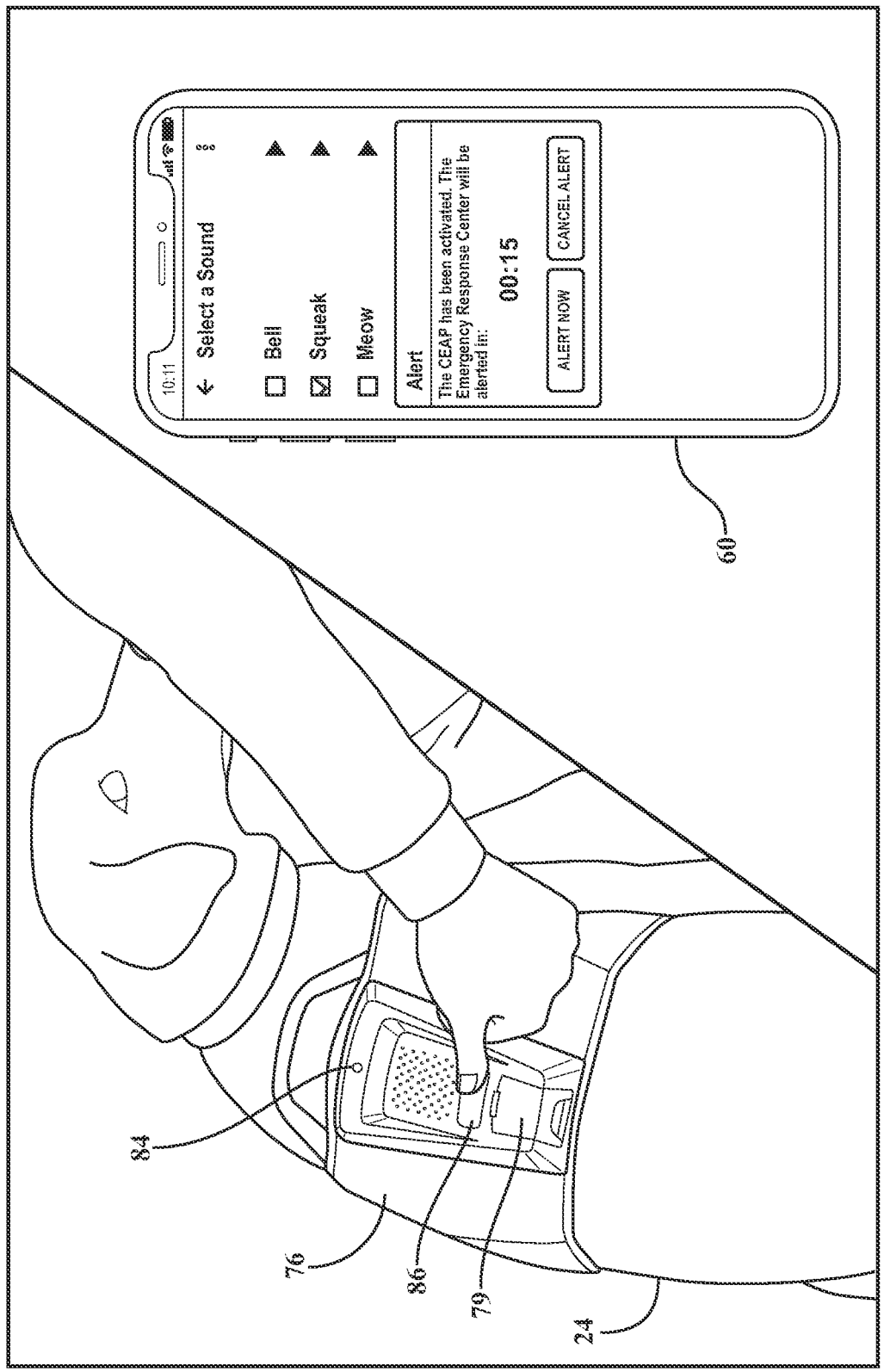
Figure 25:
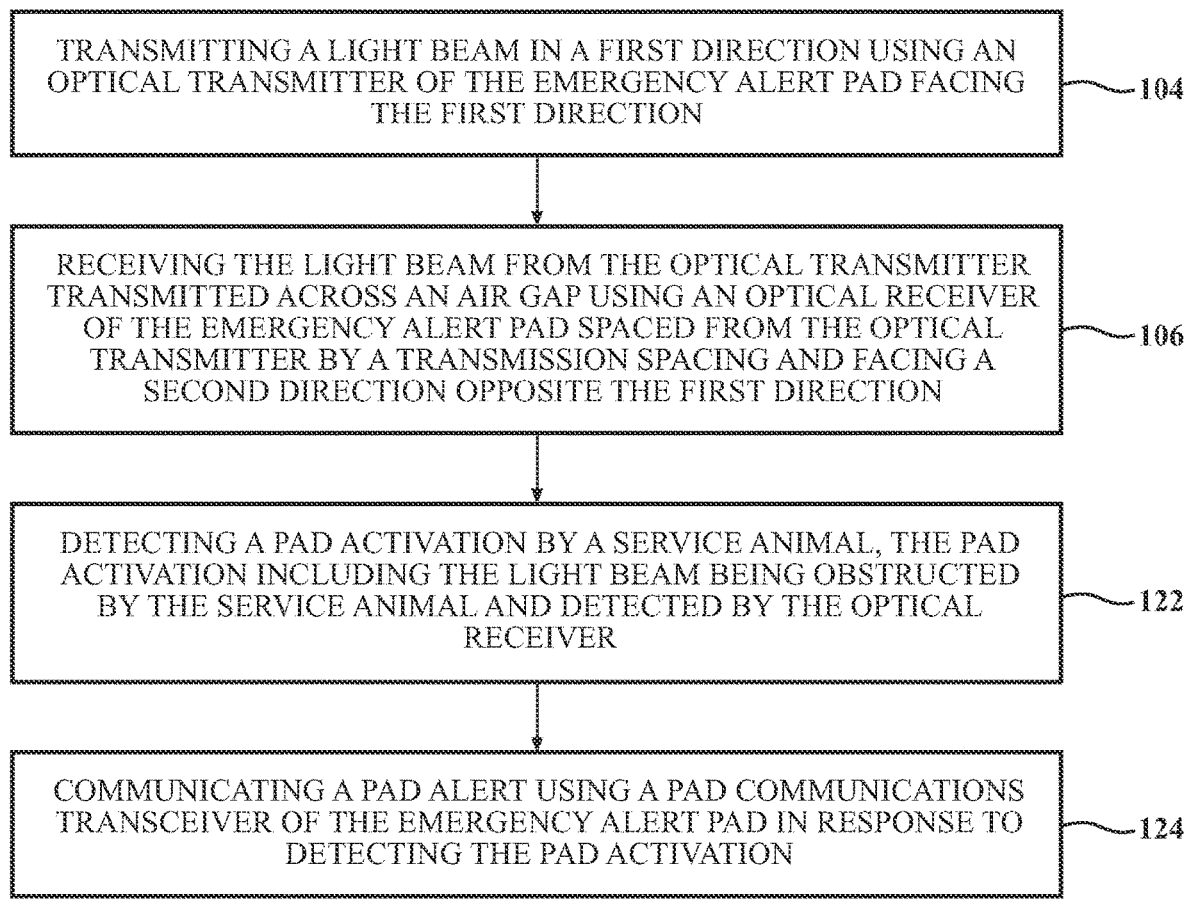
FIGS. 25 and 26A-26C illustrate steps of a method of operating the emergency alert system according to aspects of the disclosure.
Figure 26A:
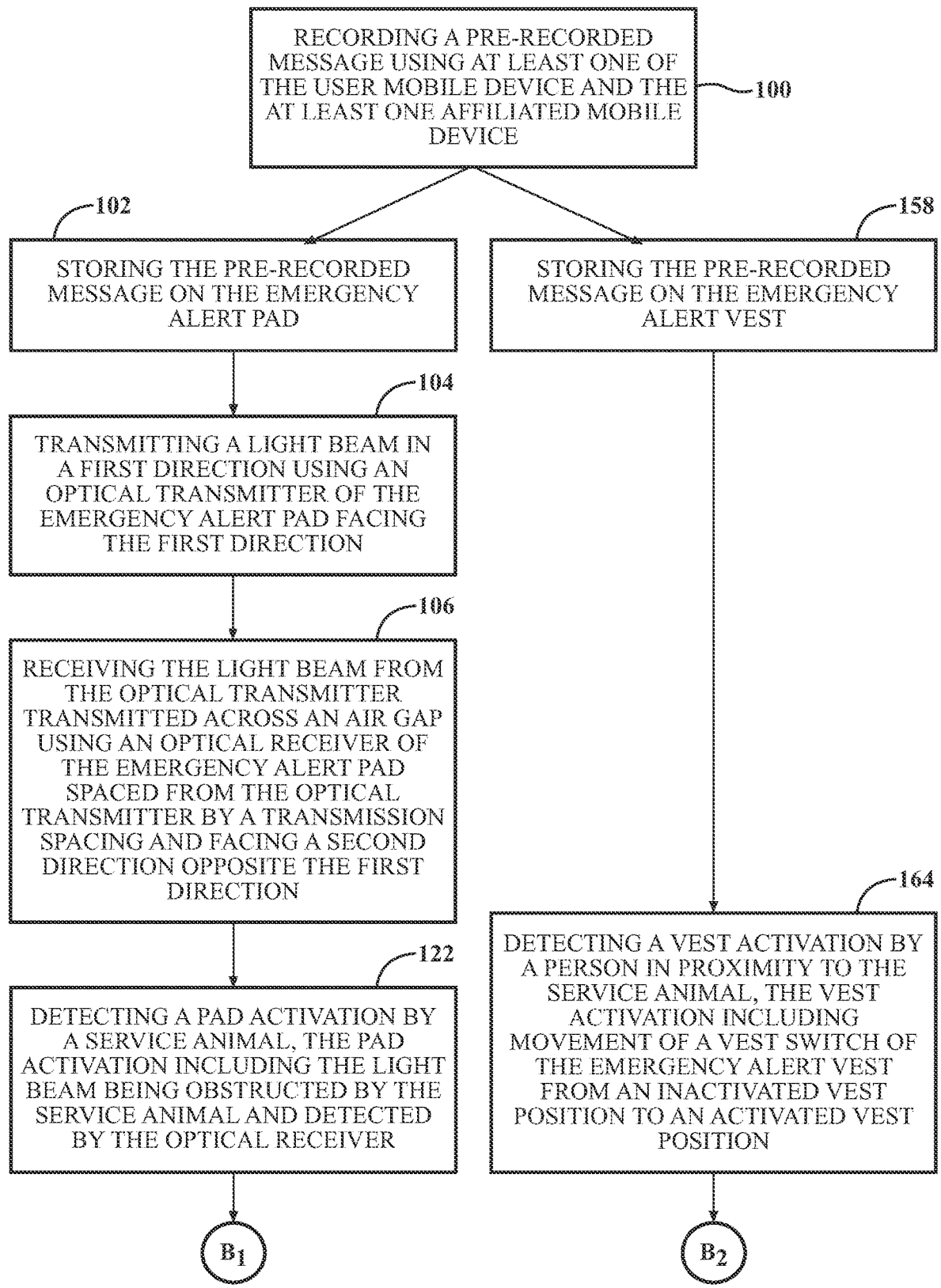
Figure 26B:
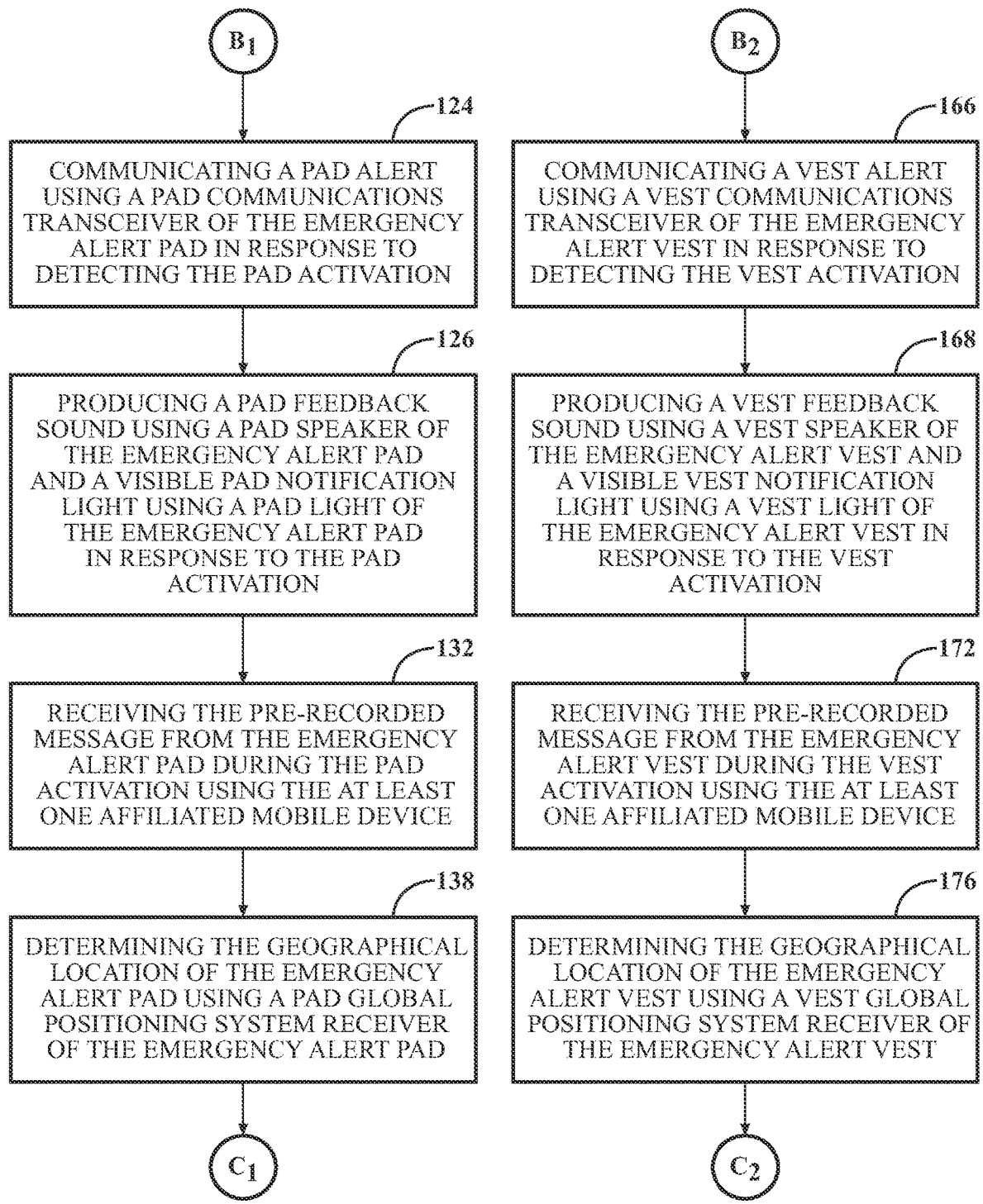
Figure 26C:
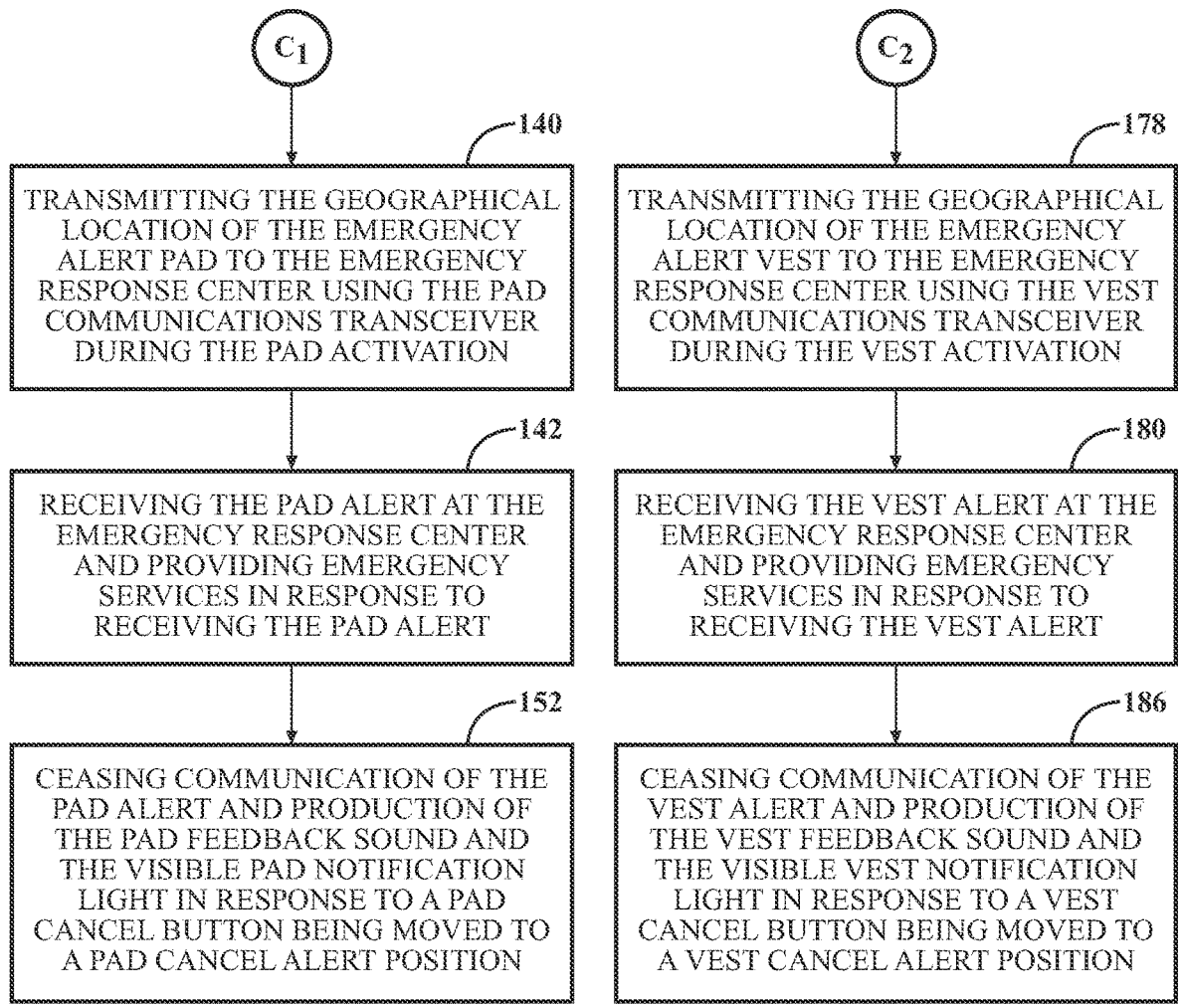

In FIG. 18, the emergency alert vest 76 is shown with the vest battery 90 charged and worn by the service animal 24 and features the vest switch 78, the vest cancel button 86, vest speaker 82, and vest light 84. The vest switch 78 is protected from accidental actuation with a protective cover 79. If the owner 65 feels a medical episode coming on, they can flip up the protective cover 79 and move the vest switch 78 on the emergency alert vest 76 from the inactivated vest position to the activated vest position, as shown in FIG. 19. Then, as best shown in FIG. 20, the emergency alert vest 76 plays the vest feedback sound (e.g., the pre-recorded message or another pre-recorded emergency recording) using the vest speaker 82 and flashes the vest light 84. As shown in FIG. 21, the vest communications transceiver 80 dials and alerts emergency contacts with the pre-recorded message. Next, in FIG. 22, the vest communications transceiver 80 of the emergency alert vest 76 dials or otherwise contacts the emergency response center 42. The response agent 72 at the emergency response center 42 accesses the owner's information and attempts to establish communication. The response agent 72 evaluates the situation and decides if emergency services are needed. As shown in FIG. 23, if emergency services are needed, the response agent 72 contacts them and communicates the geographical location of the emergency alert vest 76 (e.g., from the vest global positioning system receiver 88) and medical information of the owner 65. As shown in FIG. 24, if the emergency alert vest 76 was mistakenly activated, the vest cancel button 86 (or a popup notification or button in the mobile application on the user mobile device 60) can be pushed to cancel the vest alert.

As shown in FIGS. 25, 26A-26C, and 27-29, a method of operating the emergency alert system 20 is also provided. As discussed, the emergency alert system 20 includes the emergency alert pad 22 in communication with the user mobile device 60, the at least one affiliated mobile device 62, and the emergency response center 42. So, referring initially to FIGS. 25, 26A-26C, 27 and 28, the method includes the step of 100 recording a pre-recorded message using at least one of the user mobile device 60 and the at least one affiliated mobile device 62. The method continues with the step of 102 storing the pre-recorded message on the emergency alert pad 22. The method also includes the step of 104 transmitting a light beam in a first direction using an optical transmitter 26 of the emergency alert pad 22 facing the first direction. The method continues with the step of 106 receiving the light beam from the optical transmitter 26 transmitted across an air gap 30 sized to receive an appendage of the service animal 24 (e.g., the paw or nose of the service animal 24) using an optical receiver 28 of the emergency alert pad 22 spaced from the optical transmitter 26 by a transmission spacing 29 and facing a second direction opposite the first direction.

Figure 27:
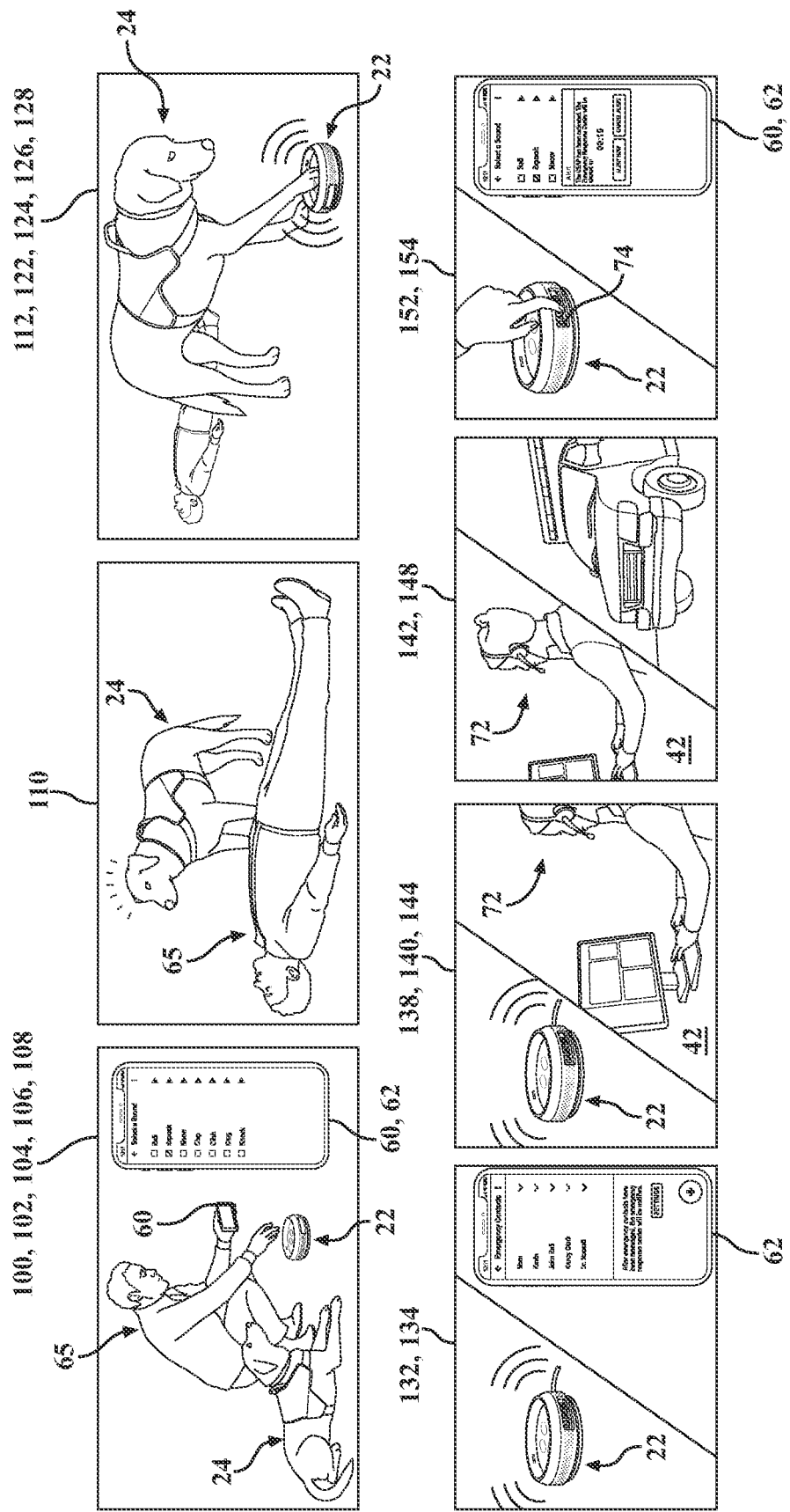
FIG. 27 shows an exemplary home use scenario including the steps of the method of FIGS. 25 and 26A-26C according to aspects of the disclosure.

Thus, in an exemplary home use scenario shown in FIG. 27, after the emergency alert pad 22 is setup and the pre-recorded message is stored on the emergency alert pad 22, the owner 65 can pick the audible pad feedback sound best suited to their service animal 24 using the mobile application on the user mobile device 60 (indicated as numeral 108 in FIG. 27). Then, as indicated with numeral 110 in FIG. 27, the trained service animal 24 is alerted to a medical emergency. As indicated with numeral 112 in FIG. 27, the service animal 24 swipes at the emergency alert pad 22.

Figure 28:
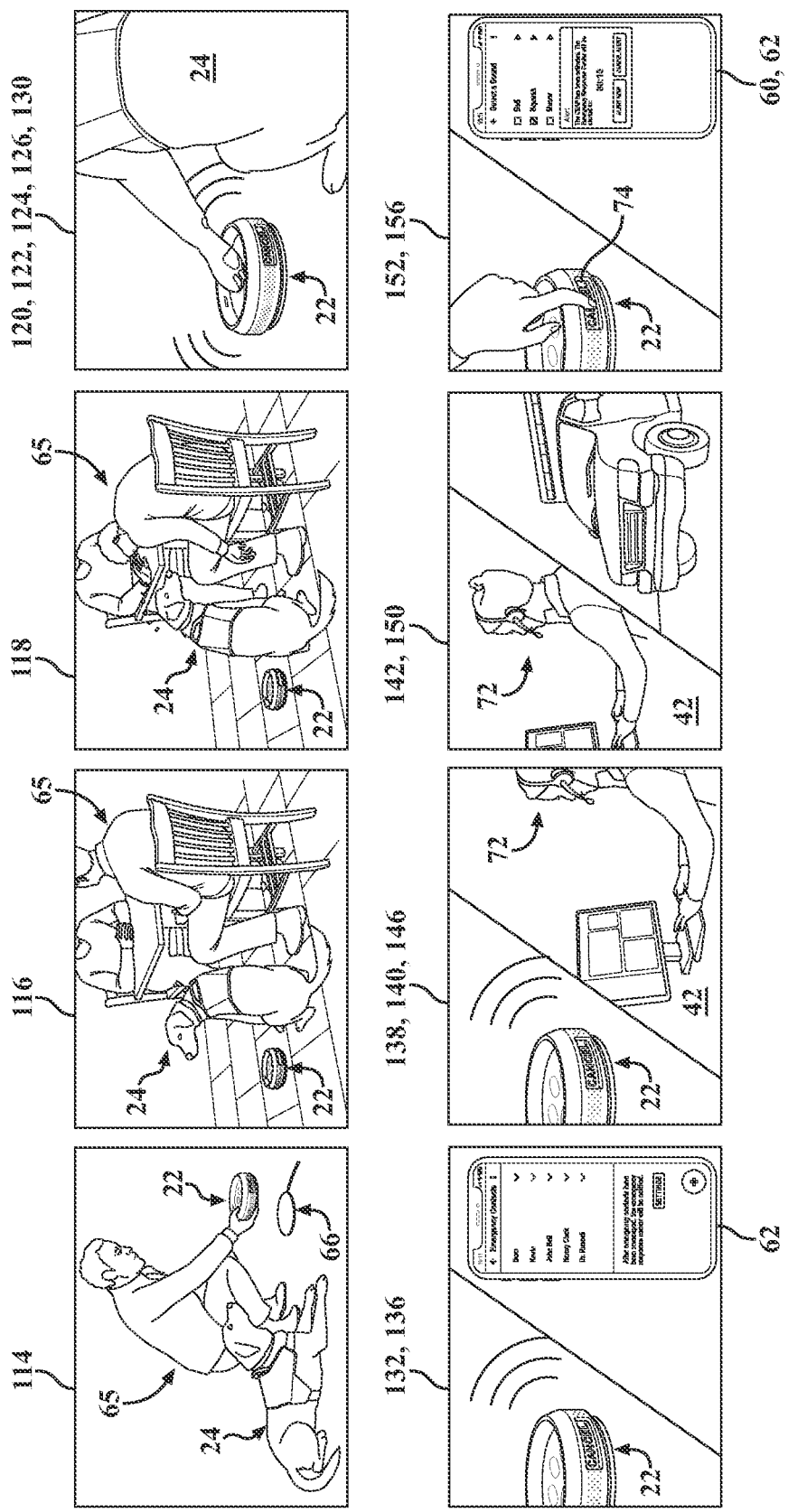
FIG. 28 shows an exemplary portable use scenario including the steps of the method of FIGS. 25 and 26A-26C according to aspects of the disclosure.
Figure 29:
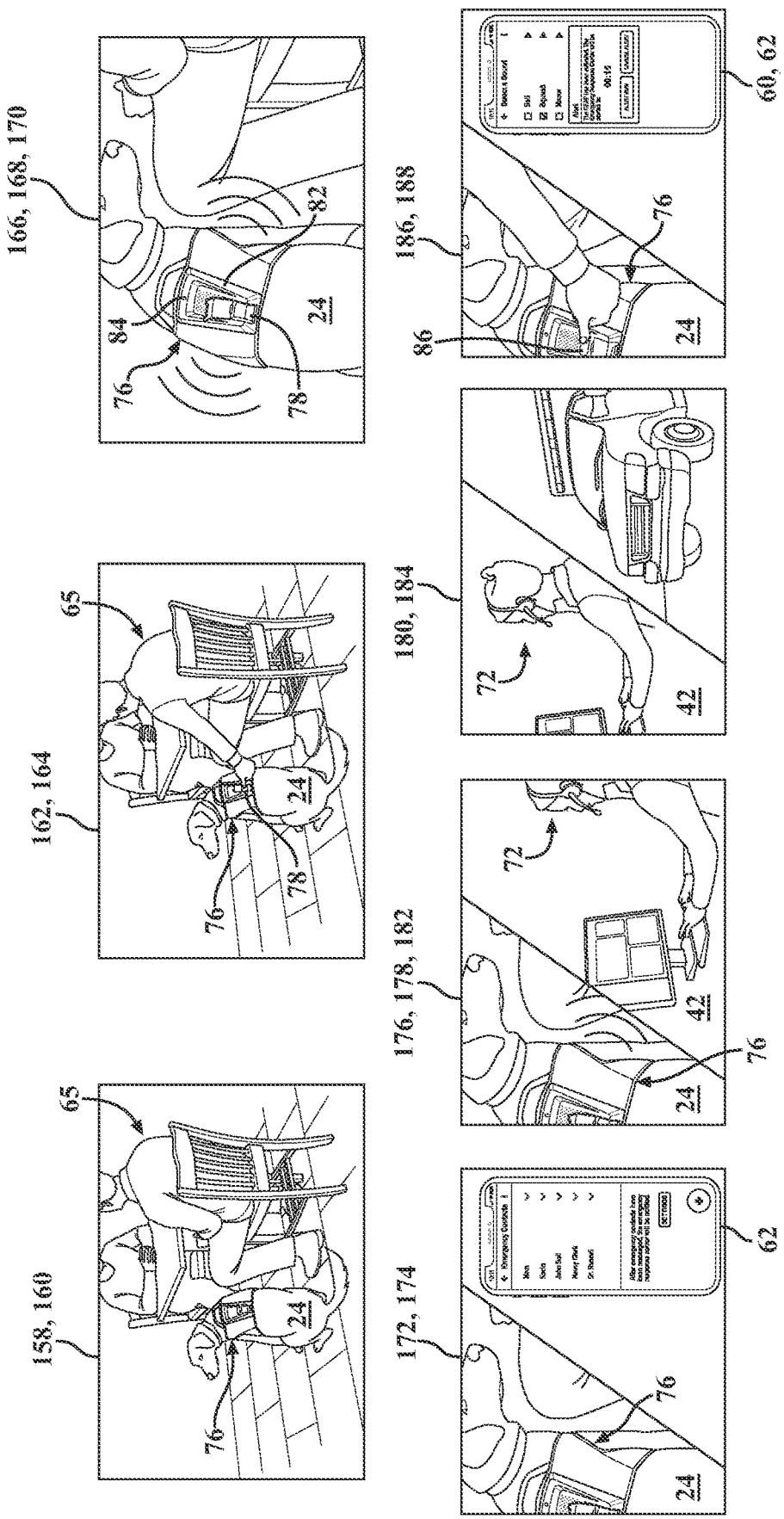
FIG. 29 shows an exemplary canine vest use scenario including the steps of the method of 26A-26C according to aspects of the disclosure.

Similarly, in an exemplary portable use scenario shown in FIG. 28, the owner 65 removes the emergency alert pad 22 from the charging dock 66 (indicated as numeral 114 in FIG. 28) and sets the emergency alert pad 22 on a floor nearby (indicated as numeral 116 in FIG. 28). Again, the pre-recorded message is stored on the emergency alert pad 22 and the owner 65 picks the audible pad feedback sound best suited to their service animal 24 using the mobile application on the user mobile device 60. Then, as indicated with numeral 118 in FIG. 28, the trained service animal 24 is alerted to a medical emergency and as indicated with numeral 120 in FIG. 28, the service animal 24 swipes at the emergency alert pad 22.

So, the next step of the method is 122 detecting a pad activation by the service animal 24, the pad activation including the light beam being obstructed by an appendage of the service animal 24 (e.g., paw, nose, etc.) and detected by the optical receiver 28. The method also includes the step of 124 communicating a pad alert using a pad communications transceiver 32 of the emergency alert pad 22 in response to detecting the pad activation. The method additionally includes the step of 126 producing a pad feedback sound using a pad speaker 68 of the emergency alert pad 22 and a visible pad notification light using a pad light 70 of the emergency alert pad 22 in response to the pad activation (indicated as numeral 128 in FIG. 27 and as numeral 130 in FIG. 28).

Still referring to FIGS. 25, 26A-26C, 27 and 28, the next step of the method is 132 receiving the pre-recorded message from the emergency alert pad 22 during the pad activation using the at least one affiliated mobile device 62. In other words, as indicated as numeral 134 in the exemplary home use scenario of FIG. 27 and numeral 136 in the exemplary portable use scenario of FIG. 28, the emergency alert pad 22 alerts the emergency contacts of the owner 65. In addition, the method includes the step of 138 determining the geographical location of the emergency alert pad 22 using a pad global positioning system receiver 40 of the emergency alert pad 22. The next step of the method is 140 transmitting the geographical location of the emergency alert pad 22 to the emergency response center 42 using the pad communications transceiver 32 during the pad activation. The method also includes the step of 142 receiving the pad alert at the emergency response center 42 and providing emergency services in response to receiving the pad alert. In more detail, as indicated as numeral 144 in the exemplary home use scenario of FIG. 27 and numeral 146 in the exemplary portable use scenario of FIG. 28, the response agent 72 at the emergency response center 42 evaluates the situation and decides if emergency services are needed. If emergency services are needed, the response agent 72 contacts them and communicates the geographical location (e.g., ascertained by the pad GPS receiver 40) and medical information, as indicated as numeral 148 in the exemplary home use scenario of FIG. 27 and numeral 150 in the exemplary portable use scenario of FIG. 28.

The method also includes the step of 152 ceasing communication of the pad alert and production of the pad feedback sound and the visible pad notification light in response to a pad cancel button 74 being moved to a pad cancel alert position. So, as indicated as numeral 154 in the exemplary home use scenario of FIG. 27 and numeral 156 in the exemplary portable use scenario of FIG. 28, pushing the pad cancel button 74 of the emergency alert pad 22 (or in the mobile application) cancels communication of the pad alert and production of the pad feedback sound and the visible pad notification light.

As discussed, the emergency alert system 20 can further include the emergency alert vest 76 worn by the service animal 24 and in communication with the user mobile device 60 and the at least one affiliated mobile device 62 and the emergency response center 42 of the emergency alert system 20. Thus, referring to FIGS. 26A-26C and 29, after the step of 100 recording the pre-recorded message using at least one of the user mobile device 60 and the at least one affiliated mobile device 62, the next step of the method is 158 storing the pre-recorded message on the emergency alert vest 76. So, in an exemplary canine vest scenario shown in FIG. 29, the service animal 24 wears the emergency alert vest 76 (after charging) (indicated as numeral 160 in FIG. 29). Then, as indicated with numeral 162 in FIG. 29, the owner 65 begins having a medical episode and moves the vest switch 78.

Thus, the method also includes the step of 164 detecting a vest activation by a person in proximity to the service animal 24 (e.g., the owner 65 or another person), the vest activation including movement of a vest switch 78 of the emergency alert vest 76 from an inactivated vest position to an activated vest position. The method continues with the step of 166 communicating a vest alert using a vest communications transceiver 80 of the emergency alert vest 76 in response to detecting the vest activation. In addition, the method also includes the step of 168 producing a vest feedback sound using a vest speaker 82 of the emergency alert vest 76 and a visible vest notification light using a vest light 84 of the emergency alert vest 76 in response to the vest activation (indicated as numeral 170 in FIG. 29).

Continuing to refer to FIGS. 26A-26C and 29, the method proceeds by 172 receiving the pre-recorded message from the emergency alert vest 76 during the vest activation using the at least one affiliated mobile device 62. In other words, as indicated as numeral 174 in the exemplary canine vest use scenario of FIG. 29, the emergency alert vest 76 alerts the emergency contacts of the owner 65. The method also includes the step of 176 determining a geographical location of the emergency alert vest 76 using a vest global positioning system receiver 88. The next step of the method is 178 transmitting the geographical location of the emergency alert vest 76 to the emergency response center 42 using the vest communications transceiver 80 during the vest activation. The next step of the method is 180 receiving the vest alert at the emergency response center 42 and providing emergency services in response to receiving the vest alert. Specifically, as indicated as numeral 182 in the exemplary canine vest use scenario of FIG. 29, the response agent 72 at the emergency response center 42 evaluates the situation and decides if emergency services are needed. If emergency services are needed, the response agent 72 contacts them and communicates the geographical location (e.g., ascertained by the vest GPS receiver 88) and medical information of the owner 65, as indicated as numeral 184 in the exemplary canine vest use scenario of FIG. 29.

The method can additionally include the step of 186 ceasing communication of the vest alert and production of the vest feedback sound and the visible vest notification light in response to a vest cancel button 86 being moved to a vest cancel alert position. So, as indicated as numeral 188 in the exemplary canine vest use scenario of FIG. 29, pushing the vest cancel button 86 of the emergency alert vest 76 (or in the mobile application) cancels communication of the vest alert and production of the vest feedback sound and the visible vest notification light.

Because the optical transmitter 26 and optical receiver 28 of the emergency alert pad 22 more easily detect the pad activation by the service animal 24 than comparable push button or momentary switch devices, there is an increased probability of successful actuation by the service animal 24 to request assistance when needed. In addition, due to such ease of operation by the service animal 24 along with the ability to select a "favorite" sound as the audible pad feedback sound, training effectiveness of the service animal 24 in operating the emergency alert pad 22 can be improved. Furthermore, due to the emergency alert vest 76 and emergency alert pad 22 employing available location and communication technology, such as Wi-Fi networking protocol, Bluetooth, and/or Long-Term Evolution (LTE) wireless broadband communication for mobile devices, and global positioning system, for example, the emergency alert pad 22, system 20, and method can therefore provide improved operational capabilities when operated by service animals 24 and/or humans 65, especially in a portable context.

Clearly, changes may be made to what is described and illustrated herein without, however, departing from the scope defined in the accompanying claims. The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," "top", "bottom", and the like, may be used herein for ease of description to describe one element's or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

What is claimed is:

1. An emergency alert pad operable by a service animal, comprising:
    an optical transmitter facing a first direction for transmitting a light beam in the first direction;
    an optical receiver spaced from the optical transmitter by a transmission spacing to define an air gap sized to receive an appendage of the service animal and facing a second direction opposite the first direction for receiving the light beam from the optical transmitter transmitted across the air gap;
    a pad communications transceiver for communicating a pad alert; and
    a pad control unit coupled to the optical transmitter and the optical receiver and the pad communications transceiver and configured to communicate the pad alert using the pad communications transceiver in response to the optical receiver detecting that the light beam has been obstructed by the appendage of the service animal.

2. The emergency alert pad as set forth in claim 1, further including a pad cancel button coupled to the pad control unit and movable between a default pad position and a pad cancel alert position when activated and wherein the pad control unit is configured to cease communication of the pad alert in response to the pad cancel button being moved to the pad cancel alert position.

3. The emergency alert pad as set forth in claim 2, including a pad housing being cylindrically shaped and having a top and a bottom and a peripheral wall extending circumferentially around and between the top and the bottom, the top including a recessed platform being circular and parallel to and spaced from the bottom and defining a recess extending into the pad housing toward the bottom a recess depth and an inner lip extending circumferentially around the recessed platform and from the recessed platform to the peripheral wall at a rim.

4. The emergency alert pad as set forth in claim 3, wherein the optical transmitter is disposed on the inner lip and configured to transmit the light beam along the recessed platform across the recess and the optical receiver is disposed on the inner lip and circumferentially spaced from the optical transmitter by 180 degrees and configured to receive the light beam from the optical transmitter.

5. The emergency alert pad as set forth in claim 3, wherein the pad cancel button is disposed on the peripheral wall.

6. The emergency alert pad as set forth in claim 1, further including a pad speaker coupled to the pad control unit for emitting an audible pad feedback sound and a pad light for emitting a visible pad notification light and wherein the pad control unit is further configured to produce the audible pad feedback sound using the pad speaker and the visible pad notification light using the pad light in response to the optical receiver detecting that the light beam has been obstructed by the appendage of the service animal.

7. The emergency alert pad as set forth in claim 1, wherein the pad control unit includes a pad processor and a pad memory in communication with the pad processor, the pad communications transceiver being in communication with at least one mobile device and the pad control unit is configured to:
    store a pre-recorded message recorded by the at least one mobile device in the pad memory, and
    transmit the pre-recorded message to a plurality of emergency contacts and communicate the pad alert to an emergency response center using the pad communications transceiver in response to the optical receiver detecting that the light beam has been obstructed by the appendage of the service animal.

8. The emergency alert pad as set forth in claim 1, further including a pad global positioning system receiver coupled to the pad control unit for ascertaining a geographical location of the emergency alert pad and wherein the pad control unit is configured to:
    determine the geographical location of the emergency alert pad, and
    transmit the geographical location of the emergency alert pad to an emergency response center using the pad communications transceiver in response to the optical receiver detecting that the light beam has been obstructed by the appendage of the service animal.

9. An emergency alert system comprising:
    an emergency alert pad configured to detect a pad activation by a service animal and communicate a pad alert in response to detecting the pad activation by the service animal;
    an emergency alert vest worn by the service animal and configured to detect a vest activation by a person in proximity to the service animal and communicate a vest alert in response to detecting the vest activation by the person in proximity to the service animal;
    a user mobile device in communication with the emergency alert pad and the emergency alert vest and configured to record a pre-recorded message stored by the emergency alert pad and the emergency alert vest;
    at least one affiliated mobile device in communication with the emergency alert pad and the emergency alert vest and configured to receive the pre-recorded message from the emergency alert pad during the pad activation and from the emergency alert vest during the vest activation; and
    an emergency response center in communication with the emergency alert pad and the emergency alert vest and configured to receive at least one of the pad alert and the vest alert and provide emergency services in response to receiving at least one of the pad alert and the vest alert.

10. The emergency alert system as set forth in claim 9, wherein the emergency alert vest includes:
    a vest switch movable between an inactivated vest position and an activated vest position when activated;
    a vest communications transceiver for communicating the vest alert;
    a vest speaker for emitting an audible vest feedback sound;
    a vest light for emitting a visible vest notification light;
    a vest cancel button movable between a default vest position and a vest cancel alert position when activated;
    a vest global positioning system receiver for ascertaining a geographical location of the emergency alert vest; and a vest control unit coupled to the vest switch and the vest communications transceiver and the vest speaker and the vest light and the vest cancel button and the vest global positioning system receiver and configured to:
   determine the geographical location of the emergency alert vest using the vest global positioning system receiver,
   communicate the vest alert and the geographical location of the emergency alert vest to the emergency response center using the vest communications transceiver in response to the vest switch being moved to the activated vest position,
   produce the audible vest feedback sound using the vest speaker and the visible vest notification light using the vest light in response to the vest switch being moved to the activated vest position, and
   cease communication of the vest alert and stop producing the audible vest feedback sound and the visible vest notification light in response to the vest cancel button being moved to the vest cancel alert position.

11. A method of operating an emergency alert system including an emergency alert pad operable by a service animal, the method comprising the steps of:
   transmitting a light beam in a first direction using an optical transmitter of the emergency alert pad facing the first direction;
   receiving the light beam from the optical transmitter transmitted across an air gap sized to receive an appendage of the service animal using an optical receiver of the emergency alert pad spaced from the optical transmitter by a transmission spacing and facing a second direction opposite the first direction;
   detecting a pad activation by the service animal, the pad activation including the light beam being obstructed by the appendage of the service animal and detected by the optical receiver; and
   communicating a pad alert using a pad communications transceiver of the emergency alert pad in response to detecting the pad activation.

12. The method as set forth in claim 11, wherein the emergency alert pad is in communication with a user mobile device and at least one affiliated mobile device and an emergency response center of the emergency alert system, the method further including the steps of:
   recording a pre-recorded message using at least one of the user mobile device and the at least one affiliated mobile device;
   storing the pre-recorded message on the emergency alert pad;
   receiving the pre-recorded message from the emergency alert pad during the pad activation using the at least one affiliated mobile device; and
   receiving the pad alert at the emergency response center and providing emergency services in response to receiving the pad alert.

13. The method as set forth in claim 12, further including the steps of:
   determining a geographical location of the emergency alert pad using a pad global positioning system receiver of the emergency alert pad, and
   transmitting the geographical location of the emergency alert pad to the emergency response center using the pad communications transceiver during the pad activation.

14. The method as set forth in claim 13, further including the step of producing a pad feedback sound using a pad speaker of the emergency alert pad and a visible pad notification light using a pad light of the emergency alert pad in response to the pad activation.

15. The method as set forth in claim 14, further including the step of ceasing communication of the pad alert and production of the pad feedback sound and the visible pad notification light in response to a pad cancel button being moved to a pad cancel alert position.

16. The method as set forth in claim 11, wherein the emergency alert system further includes an emergency alert vest worn by the service animal, the method further including the steps of:
   detecting a vest activation by a person in proximity to the service animal, the vest activation including movement of a vest switch of the emergency alert vest from an inactivated vest position to an activated vest position; and
   communicating a vest alert using a vest communications transceiver of the emergency alert vest in response to detecting the vest activation.

17. The method as set forth in claim 16, wherein the emergency alert vest is in communication with a user mobile device and at least one affiliated mobile device and an emergency response center of the emergency alert system, the method further including the steps of:
   recording a pre-recorded message using at least one of the user mobile device and the at least one affiliated mobile device;
   storing the pre-recorded message on the emergency alert vest;
   receiving the pre-recorded message from the emergency alert vest during the vest activation using the at least one affiliated mobile device; and
   receiving the vest alert at the emergency response center and providing emergency services in response to receiving the vest alert.

18. The method as set forth in claim 17, further including the steps of:
   determining a geographical location of the emergency alert vest using a vest global positioning system receiver; and
   transmitting the geographical location of the emergency alert vest to the emergency response center using the vest communications transceiver during the vest activation.

19. The method as set forth in claim 16, further including the step of producing a vest feedback sound using a vest speaker of the emergency alert vest and a visible vest notification light using a vest light of the emergency alert vest in response to the vest activation.

20. The method as set forth in claim 19, further including the step of ceasing communication of the vest alert and production of the vest feedback sound and the visible vest notification light in response to a vest cancel button being moved to a vest cancel alert position.

* * * * *